United States Patent
Hornung et al.

(10) Patent No.: US 7,052,742 B1
(45) Date of Patent: May 30, 2006

(54) FIVE MEMBERED-RING COMPOUNDS AND UTILIZATION THEREOF IN LIQUID CRYSTAL MIXTURES

(75) Inventors: Barbara Hornung, Hasselroth (DE); Toshiaki Nonaka, Kakegawa (JP); Ayako Ogawa, Kakegawa (JP); Wolfgang Schmidt, Dreieich (DE); Rainer Wingen, Hattersheim (DE)

(73) Assignee: Clariant International Ltd., Muttenz (CH)

( * ) Notice: Subject to any disclaimer, the term of this patent is extended or adjusted under 35 U.S.C. 154(b) by 46 days.

(21) Appl. No.: 10/070,242

(22) PCT Filed: Aug. 31, 2000

(86) PCT No.: PCT/EP00/08518

§ 371 (c)(1),
(2), (4) Date: Oct. 15, 2002

(87) PCT Pub. No.: WO01/16131

PCT Pub. Date: Mar. 8, 2001

(30) Foreign Application Priority Data

| Sep. 1, 1999 | (DE) | 199 41 649 |
| Sep. 1, 1999 | (DE) | 199 41 650 |
| Sep. 1, 1999 | (DE) | 199 41 651 |
| Sep. 1, 1999 | (DE) | 199 41 653 |
| Sep. 1, 1999 | (DE) | 199 41 654 |
| Sep. 1, 1999 | (DE) | 199 41 656 |

(51) Int. Cl.
*C09K 19/34* (2006.01)
*C09K 19/30* (2006.01)
*C07D 333/02* (2006.01)
*C07D 307/34* (2006.01)
*C07D 261/06* (2006.01)

(52) U.S. Cl. ............ 428/1.1; 252/299.61; 252/299.63; 252/299.66; 252/299.67; 548/146; 548/182; 548/240; 548/243; 548/247; 549/29; 549/475

(58) Field of Classification Search ................. 428/1.1; 252/299.01, 299.61, 299.66, 299.67; 548/146, 548/182, 188, 240, 243, 247; 549/29, 475
See application file for complete search history.

(56) References Cited

U.S. PATENT DOCUMENTS 4,873,019 A 10/1989 Krause et al. ......... 252/299.61
4,988,701 A * 1/1991 Di Domenico et al. .. 514/253.1

FOREIGN PATENT DOCUMENTS

| DE | 44 46 836 A1 | 6/1995 |
| DE | 197 40 898 A1 | 3/1998 |
| DE | 197 48 432 A1 | 5/1999 |
| EP | 0 032 362 A1 | 7/1981 |
| EP | 0 364 923 A2 | 4/1990 |
| EP | 0 439 170 B1 | 7/1991 |
| EP | 0 500 072 A1 | 8/1992 |
| EP | 0 916 714 A1 | 5/1999 |
| GB | 2 229 179 A | 9/1990 |
| JP | 63-60981 | 3/1988 |
| JP | 10-333113 | 12/1998 |
| JP | 2000017264 | * 1/2000 |

OTHER PUBLICATIONS

CAPLUS 2001: 133368.*
CA 130: 124916.*
CA 130: 3810.*
CA 129: 175594.*
CA: 125: 10674.*
CA 108: 150363.*
CA 102: 95576.*
CA 96: 52210.*
CA 89: 197380.*
CA 87: 39344.*
CA 78: 97536.*
CA 73: 45428.*
English translation by computer for JP 2000-17264, http://www4.ipdl.ncipi.go.jp/Tokujitu/PAJdetail.ipdl?N0000=60&N0120=01&N2001=2&N3001=2000-017264.*
J. W Brown et al., "Some Three-Ring Esters Containing a Five-Membered Heteroaromatic Ring. A Comparison of Liquid Crystal Properties", Molecular Crystals and Liquid Crystals, 1989, vol. 173 pp. 121-140.

(Continued)

*Primary Examiner*—Shean C. Wu
(74) *Attorney, Agent, or Firm*—Frommer Lawrence & Haug LLP

(57) ABSTRACT

Fluorinated five-membered ring compounds of the formula (I)

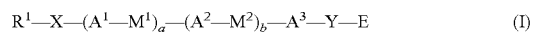

where E is a radical T—Z—$R^2$ containing a five-membered ring and, for example,
T is undirected and is 4-fluorothiophene-2,5-diyl, 3-fluorothiophene-2,5-diyl, 3-fluorothiophene-2,4-diyl, 5-fluorothiophene-2,4-diyl, furan-2,5-diyl, furan-2,4-diyl, isoxazole-3,5-diyl, thiazole-2,5-diyl, thiazole-2,4-diyl, cyclopentane-1,3-diyl or cyclopentene-1,3-diyl,
$R^1$ and $R^2$ are hydrogen,
X is a single bond, —O—, OC(=O)—, —C(=O)O— or —OC(=O)O—,
Y is —OC(=O)—, —OCH$_2$—, —CH$_2$CH$_2$—,
Z is a single bond or —O—,
$A^1$, $A^2$, $A^3$ are each, independently of one another, phenylene-1,4-diyl,
$M^1$, $M^2$ are undirected and are each, independently of one another, —OC(=O)—, —OCH$_2$—, —CH$_2$CH$_2$—, —OC(=O)CH$_2$CH$_2$—, —OCH$_2$CH$_2$—, —C≡C—, —CH$_2$CH$_2$CH$_2$CH$_2$— or a single bond,
a, b are each, independently of one another, 0 or 1,
are used in FLC mixtures.

12 Claims, No Drawings

OTHER PUBLICATIONS

M. Osman. et al. "Stable Liquid Crystals with Large Negative Dielectric Anisotropy—III", Molecular Crystals and Liquid Crystals, (Letters). 1983, vol. 82, pp. 339-344.

D.F. Andres. "Reaction of Thioglycolate with α-Fluoro-β-(Phenylthio)enones (or-enals): Synthesis of Substituted β-Carboxy-γ-Fluorothiophenes". 1997. Tetrahedron Letters. vol. 38, No. 6. pp. 1049-1052.

C. Corral et al., "The Behavior of Vicinal Alkyl Aminothiophene-carboxylates in the Sandmeyer and Schiemann Reactions", 1985, Heterocycles. vol. 23, No. 6. pp. 1431-1435.

S. Takenaka et al., The $S_A$-$S_A$ Transition in a Homologous Series of 4(4-Alkoxyphenoxycarbonyl)phenyl 5-Nitro-2-furancarbolylates, 1985. Molecular Crystals and Liquid Crystals. vol. 131. No. 3/4.

* cited by examiner

FIVE MEMBERED-RING COMPOUNDS AND UTILIZATION THEREOF IN LIQUID CRYSTAL MIXTURES

Besides nematic and cholesteric liquid crystals, optically active, tilted smectic (ferroelectric) liquid crystals have also recently been used in commercial display devices.

Clark and Lagerwall have been able to show that the use of ferroelectric liquid crystals (FLCs) in very thin cells results in opto-electrical switching or display elements which have response times which are of up to 1000 times faster than conventional TN ("twisted nematic") cells (see, for example, EP-A 0 032 362). Owing to this and other favorable properties, for example the possibility of bistable switching and the virtually viewing angle-independent contrast, FLCs are basically highly suitable for areas of application such as computer displays.

For a more detailed discussion of the technical requirements of FLCs, reference is made to European Patent Application 97118671.3 and DE-A 197 48 432.

Thiophene derivatives have already been described for use in liquid-crystal mixtures, e.g. in EP-B 0 500 072. Some 3- or 4-fluorothiophenecarboxylic acids have also been described, e.g. in Tetrahedron Letters 1997, 38(6), 1049; Heterocycles 23, 1431 (1985); Synth. Commun. 24, 95 (1994). However, these latter documents do not indicate any suitability for use as a building block for liquid crystals.

JP-A 6306098 describes esters of furanacrylic acid having terminally polar phenols for use in nemtic liquid-crystal mixtures.

JP-A 10-333113 describes 3,5-diarylisoxazoles for use in ferroelectric liquid-crystal mixtures, especially operated in inverse mode. 2,5-Diarylthiazoles for use in ferroelectric liquid-crystal mixtures are described, for example, in EP-B 0 439 170.

Cyclopentane derivatives have previously been described in general for use in liquid-crystal mixtures in U.S. Pat. No. 4,873,019; however, this document does not suggest to the person skilled in the art that the compounds of the formula (II) encompassed by the general formula of this document are particularly suitable as components of chiral smectic liquid-crystal mixtures.

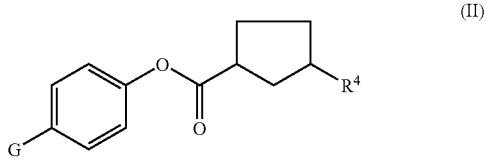

(II)

in which $R^4$ is as defined below

G is F or CN or trans-4-propyl-cyclohexyl or trans-4-butyl-cyclohexyl or an alkyl radical of 1 to 15 carbon atoms, in which one or more nonadjacent $CH_2$ groups may be replaced by —O—, —CO—, —OCO—, —O—CO—O—, —CHhalogen-, —CHCN— and/or —CH=CH—.

However, since the development, in particular of ferroelectric liquid-crystal mixtures, can in no way be regarded as complete, display manufacturers are interested in a wide variety of components for mixtures, partly because only the interaction of the liquid-crystalline mixtures with the individual components of the display device or of the cells (for example the alignment layer) allows conclusions to be drawn on the quality of the liquid-crystalline mixtures.

It has now been found that five-membered ring compounds of the formula (I), even when admixed in small amounts, have a favorable effect on the properties of liquid-crystal mixtures, in particular chiral smectic mixtures, for example regarding the dielectric anisotropy and/or the melting point, but also regarding the switching behavior, the tilt angle values and the temperature dependence of the tilt angle.

The invention therefore provides five-membered ring compounds of the formula (I),

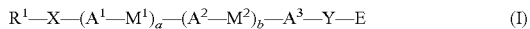

$$R^1—X—(A^1—M^1)_a—(A^2—M^2)_b—A^3—Y—E \qquad (I)$$

where the symbols and indices have the following meanings:
E is a radical $T—Z—R^2$ containing a five-membered ring, where:

(i) T is undirected and is 4-fluorothiophene-2,5-diyl, 3-fluorothiophene-2,5-diyl, 3-fluorothiophene-2,4-diyl or 5-fluorothiophene-2,4-diyl
  Z is a single bond or —O—
  $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, with the provisos that
    a) the —$CH_2$— group nearest to the thiophene cannot be replaced by —O— when Z is —O—
    b) $R^2$ can only be hydrogen when Z is a single bond, (ii) T is furan-2,5-diyl or furan-2,4-diyl
  Z is a single bond or —O—
  $R^2$ is hydrogen or a straight-chain or branched alkyl radical (with or without asymmetric carbon atoms) having 1 to 20 carbon atoms, where one nonterminal $CH_2$ group nonadjacent to furan may be replaced by —O— or —OC(=O)— or —C(=O)O— and/or one or more H atoms may be replaced by F, (iii) T is undirected and is isoxazole-3,5-diyl
  Z is a single bond or —O—
  $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, with the provisos that
    a) the —$CH_2$— group nearest to the isoxazole cannot be replaced by —O— when Z is —O—
    b) $R^2$ can only be hydrogen when Z is a single bond, (iv) T is undirected and is thiazole-2,5-diyl or thiazole-2,4-diyl
  Z is a single bond
  $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, (v) T is cyclopentane-1,3-diyl
  Z is a single bond or —O—
  $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, with the provisos that a) the —CH$_2$— group nearest to the cyclopentane cannot be replaced by —O— when Z is —O—
b) R$^2$ can only be hydrogen when Z is a single bond, with the exception of compounds of the formula (II)

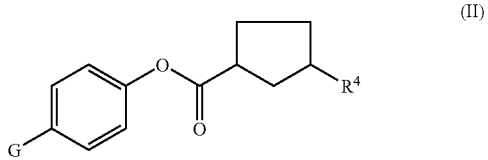

(II)

in which
R$^4$ is as defined for R$^2$
G is trans-4-propyl-cyclohexyl or trans-4-butyl-cyclohexyl or an alkyl group of 1 to 15 carbon atoms, in which, in addition, one or more nonadjacent CH$_2$ groups may be replaced by —O—, —CO—, —OCO—, —O—CO—O—, -CHhalogen-, —CHCN— and/or —CH=CH— or is F, CN,
(vi) T is cyclopentane-1,3-diyl, in which one —CH$_2$CH$_2$— or —CH$_2$CH— group is replaced by a —CH=CH— or CH=C— group respectively
Z is a single bond
R$^2$ is hydrogen or a straight-chain or branched alkyl radical (with or without asymmetric carbon atoms) having 1 to 20 carbon atoms, where one nonterminal CH$_2$ group may be replaced by —O— or —OC(=O)— or —C(=O)O— and/or one or more H atoms may be replaced by F, with the proviso that the —CH$_2$— group nearest to the cyclopentene cannot be replaced and where
Y cannot be —CH$_2$—CH$_2$—,
R$^1$ is hydrogen or a straight-chain or branched C$_{1-20}$-alkyl or C$_{2-20}$-alkenyl radical (with or without asymmetric carbon atoms), where
a) one or two nonterminal CH$_2$ groups may be replaced, independently of one another, by —O— or —C(=O)—, with the proviso that two adjacent CH$_2$ groups cannot be replaced in the same way, and/or
b) one CH$_2$ group may be replaced by —C≡C—, and/or
c) one CH$_2$ group may be replaced by —Si(CH$_3$)$_2$—, cyclopropane-1,2-diyl, cyclobutane-1,3-diyl, cyclopentane-1,4-diyl, bicyclo [1.1.1]pentane-1,3-diyl or cyclohexane-1,4-diyl, and/or
d) one or more H atoms may be replaced by F and/or CN,
e) in the case of a branched alkyl radical containing asymmetric carbon atoms, the asymmetric carbon atoms have —CH$_3$, —OCH$_3$, —CF$_3$, F, CN and/or Cl as substituents or
   are incorporated into a 3- to 7-membered ring, in which, in addition, one or two non-adjacent CH$_2$ groups may be replaced by —O— and one CH$_2$ group non-adjacent to these groups may be replaced by —OC(=O)—;
X is a single bond, —O—, OC(=O)—, —C(=O)O— or —OC(=O)O—
Y is —OC(=O)—, —OCH$_2$—, —CH$_2$CH$_2$—
A$^1$, A$^2$, A$^3$ are each, independently of one another, phenylene-1,4-diyl, unsubstituted or disubstituted by CN or F, phenylene-1,3-diyl, unsubstituted or monosubstituted or disubstituted by CN or F, cyclohexane-1,4-diyl, in which one or two H atoms may be replaced by CN and/or CH$_3$ and/or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, cyclopentane-2,5-diyl or thiophene-2,5-diyl;
M$^1$, M$^2$ are undirected and are each, independently of one another, —OC(=O)—, —OCH$_2$—, —CH$_2$CH$_2$—, —OC(=O)CH$_2$CH$_2$—, —OCH$_2$CH$_2$CH$_2$—, —C≡C—, —CH$_2$CH$_2$CH$_2$CH$_2$— or a single bond;
a, b are each, independently of one another, 0 or 1.

The term "terminal" means, for example in R$^1$, the CH$_2$ groups connected to X or to H. The term "undirected" means that incorporation of the group in the form of its mirror image is possible.

The five-membered ring compounds of the formula (I) are fluorinated thiophene derivatives (i), furan derivatives (ii), isoxazole derivatives (iii), thiazole derivatives (iv), cyclopentane derivatives (v) or cyclopentene derivatives (vi).

In one embodiment of the invention, one or more of the following provisos apply:

For thiophene derivatives (i), A$^1$, A$^2$, A$^3$ are not cyclopentane-2,5-diyl.

For furan derivatives, A$^1$, A$^2$, A$^3$ are not cyclopentane-2,5-diyl.

For isoxazole derivatives, A$^1$, A$^2$, A$^3$ are not cyclopentane-2,5-diyl.

For thiazole derivatives, A$^1$, A$^2$, A$^3$ are not cyclopentane-2,5-diyl.

For cyclopentane derivatives, A$^1$, A$^2$, A$^3$ are not thiophene-2,5-diyl.

For cyclopentene derivatives, cyclopentane-1,4-diyl is replaced by cyclopentane-1,3-diyl for R$^1$ in proviso c).

Fluorinated Thiophene Derivatives

Preferred thiophene derivatives (i) are the following compounds of the formulae (I-1) to (I-33)

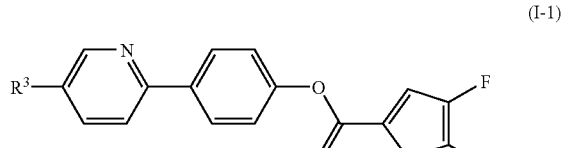

(I-1)

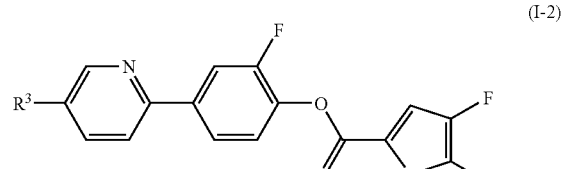

(I-2)

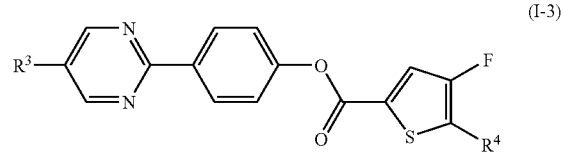

(I-3)

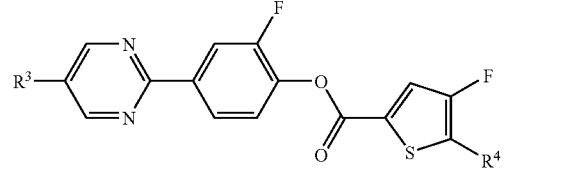

(I-4)

-continued
(I-5)
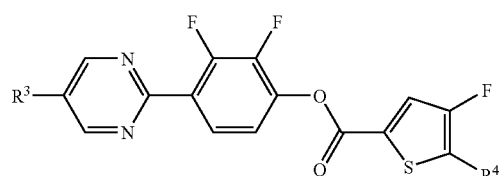
(I-6)
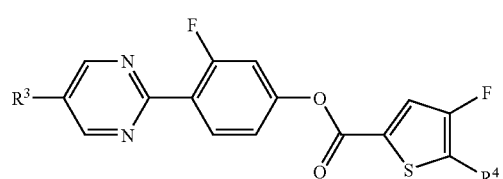
(I-7)
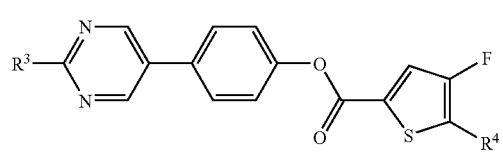
(I-8)
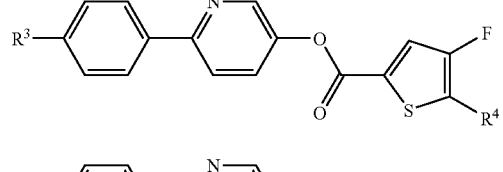
(I-9)
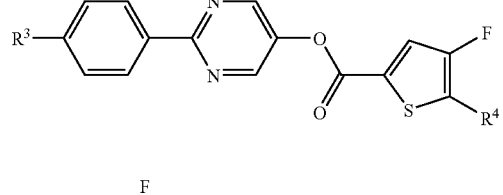
(I-10)
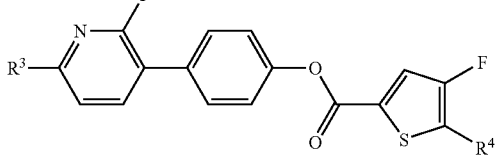
(I-11)
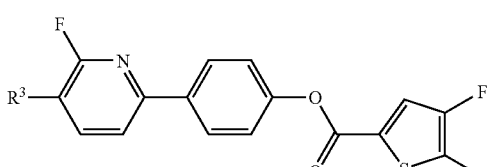
(I-12)
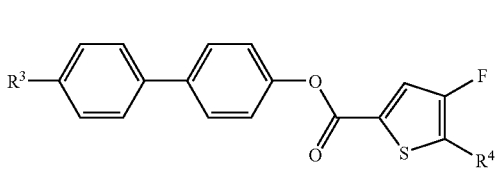
(I-13)
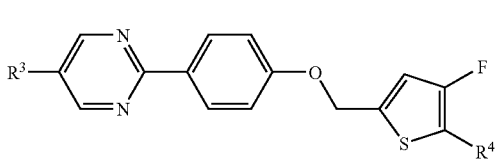
-continued
(I-14)
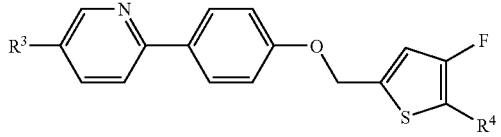
(I-15)
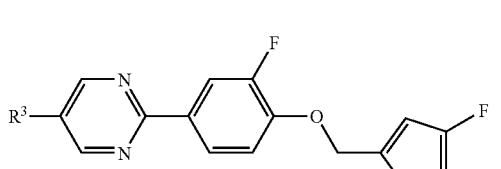
(I-16)
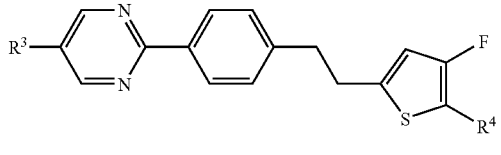
(I-17)
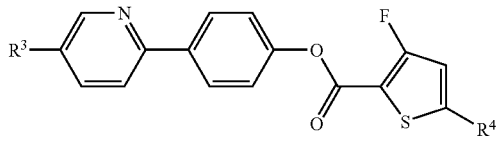
(I-18)
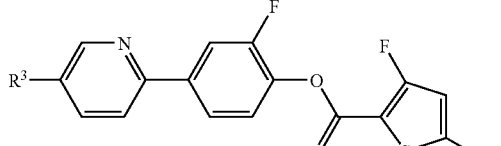
(I-19)
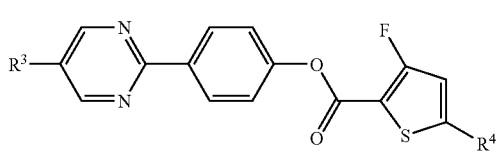
(I-20)
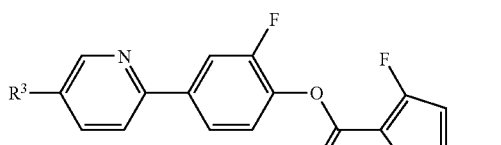
(I-21)
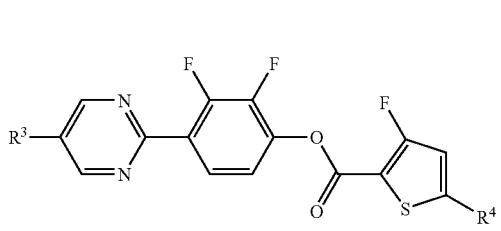

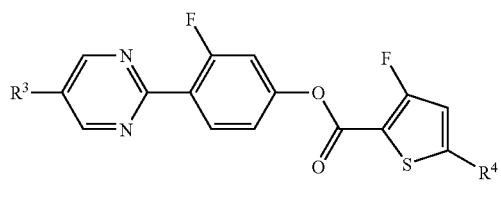
(I-23)

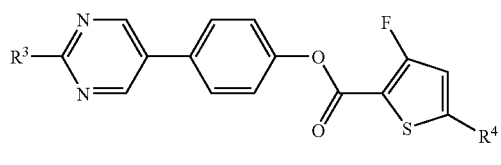
(I-24)

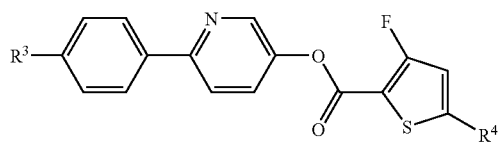
(I-25)

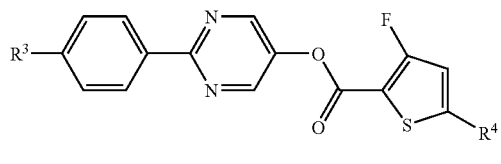
(I-26)

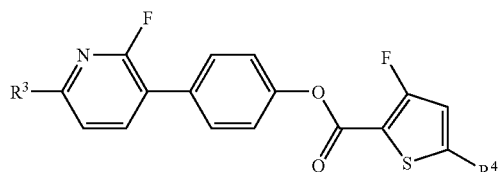
(I-27)

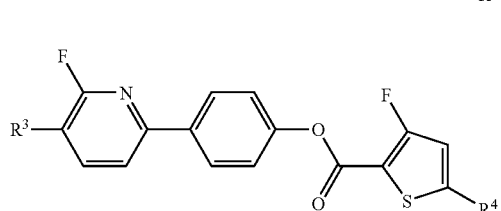
(I-28)

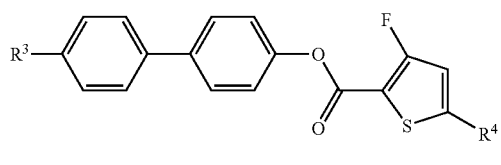
(I-29)

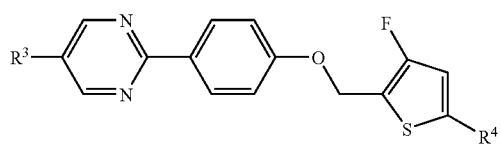
(I-30)

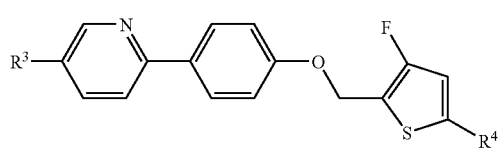
(I-31)

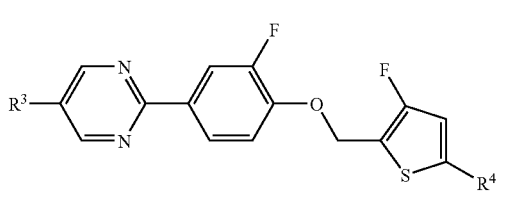
(I-32)

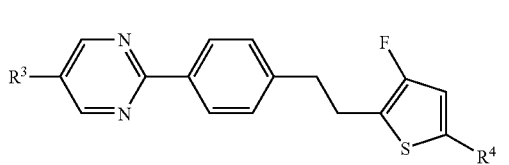
(I-33)

in which:

$R^3$ is hydrogen or a straight-chain or branched alkyl radical (with or without asymmetric carbon atoms) having 1 to 16 carbon atoms, where one nonterminal $CH_2$ group may, in addition, be replaced by —O— or, undirected, by —OC(=O)— and one or more H atoms may be replaced by F;

$R^4$ is hydrogen or a straight-chain or branched alkyl radical (with or without asymmetric carbon atoms) having 1 to 16 carbon atoms.

Particular preference is given to compounds of the formulae (I), in particular (I-1) to (I-33), in which $R^3$ and $R^4$ are each, independently of one another, a straight-chain alkyl radical having 2 to 16 carbon atoms.

Particular preference is likewise given to compounds of the formula (I), in particular (I-1) to (I-33), in which $R^3$ is a straight-chain alkoxy radical having 2 to 12 carbon atoms and $R^4$ is hydrogen or a straight-chain alkyl radical having 2 to 12 carbon atoms.

Furan Derivatives

Preferred furan derivatives (ii) are the following compounds of the formulae (I-1) to (I-16)

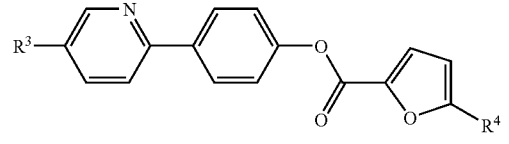
(I-1)

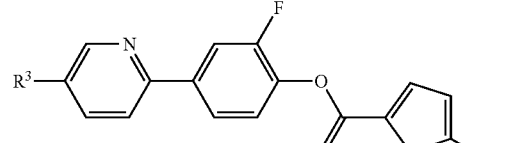
(I-2)

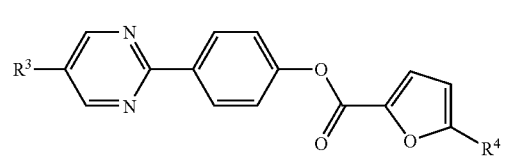
(I-3)

-continued

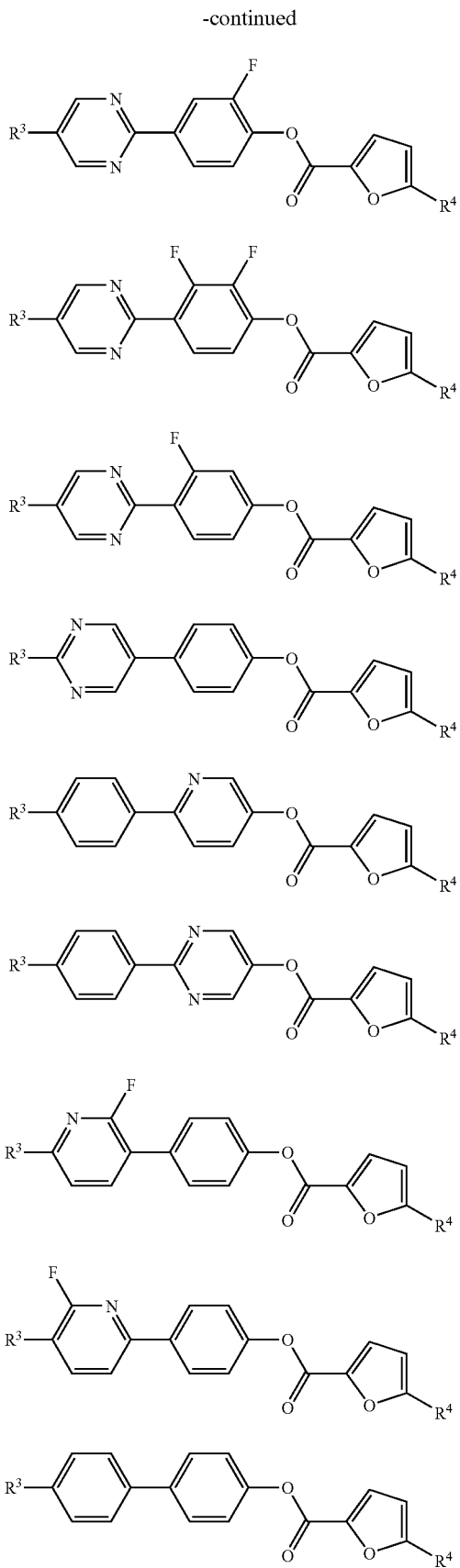

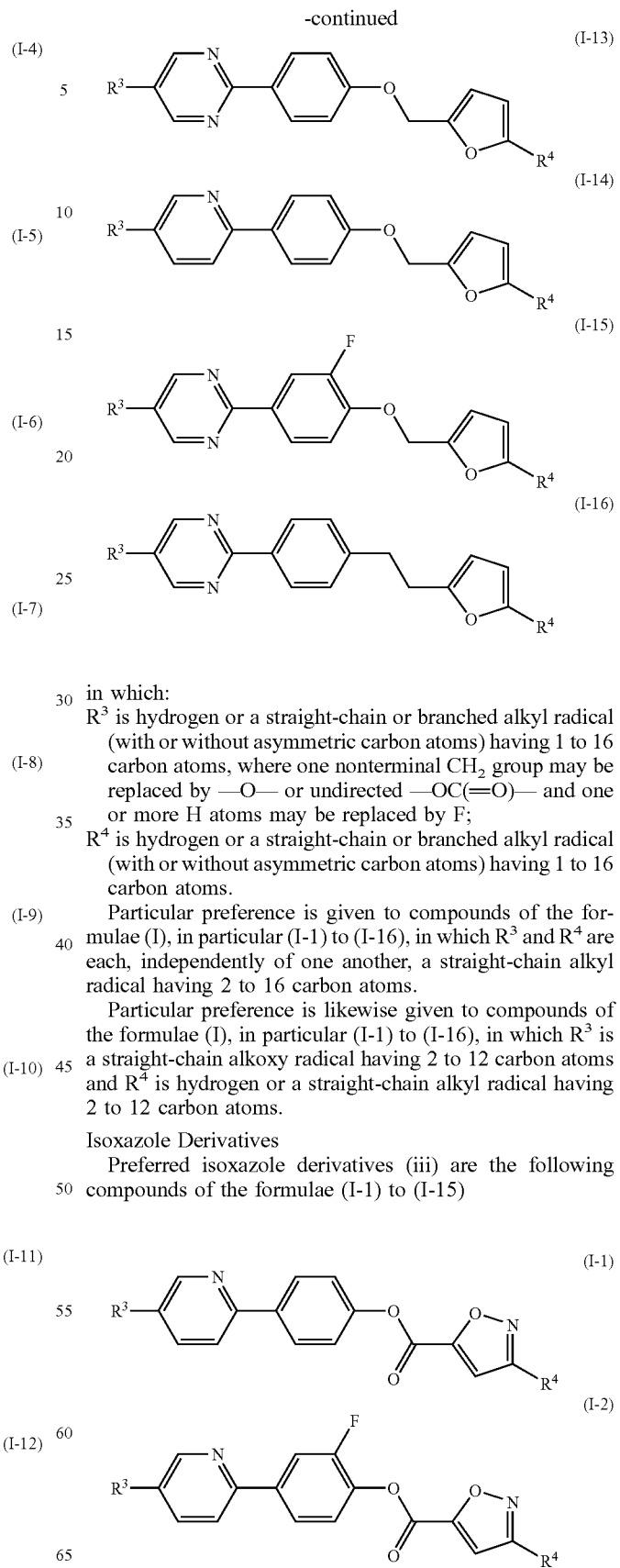

in which:
R³ is hydrogen or a straight-chain or branched alkyl radical (with or without asymmetric carbon atoms) having 1 to 16 carbon atoms, where one nonterminal CH₂ group may be replaced by —O— or undirected —OC(=O)— and one or more H atoms may be replaced by F;
R⁴ is hydrogen or a straight-chain or branched alkyl radical (with or without asymmetric carbon atoms) having 1 to 16 carbon atoms.

Particular preference is given to compounds of the formulae (I), in particular (I-1) to (I-16), in which R³ and R⁴ are each, independently of one another, a straight-chain alkyl radical having 2 to 16 carbon atoms.

Particular preference is likewise given to compounds of the formulae (I), in particular (I-1) to (I-16), in which R³ is a straight-chain alkoxy radical having 2 to 12 carbon atoms and R⁴ is hydrogen or a straight-chain alkyl radical having 2 to 12 carbon atoms.

Isoxazole Derivatives

Preferred isoxazole derivatives (iii) are the following compounds of the formulae (I-1) to (I-15)

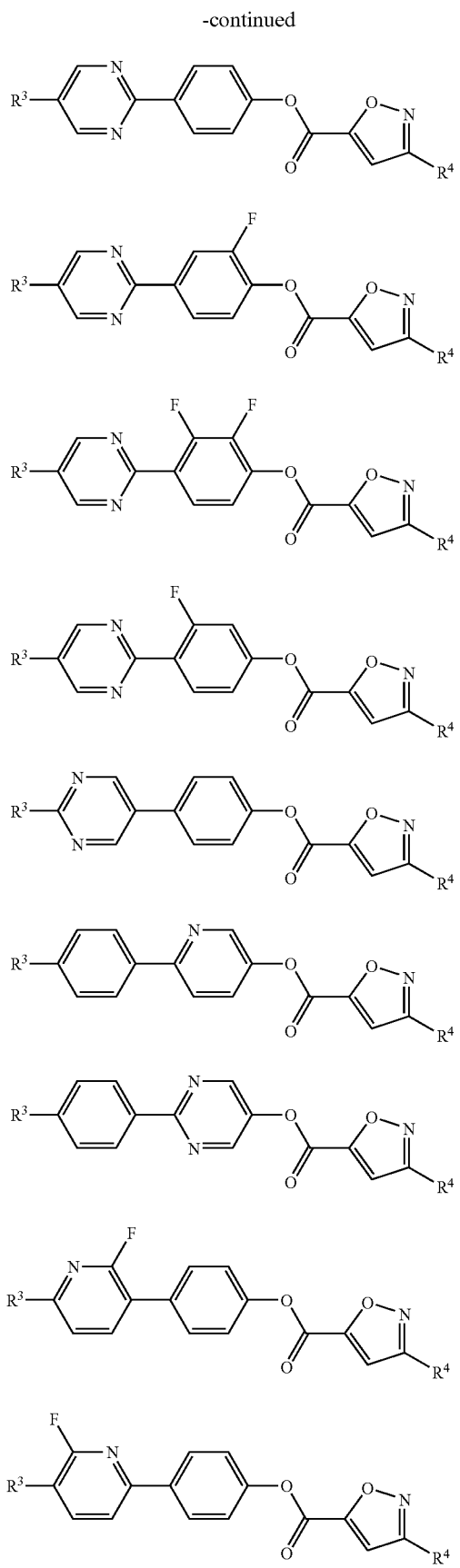
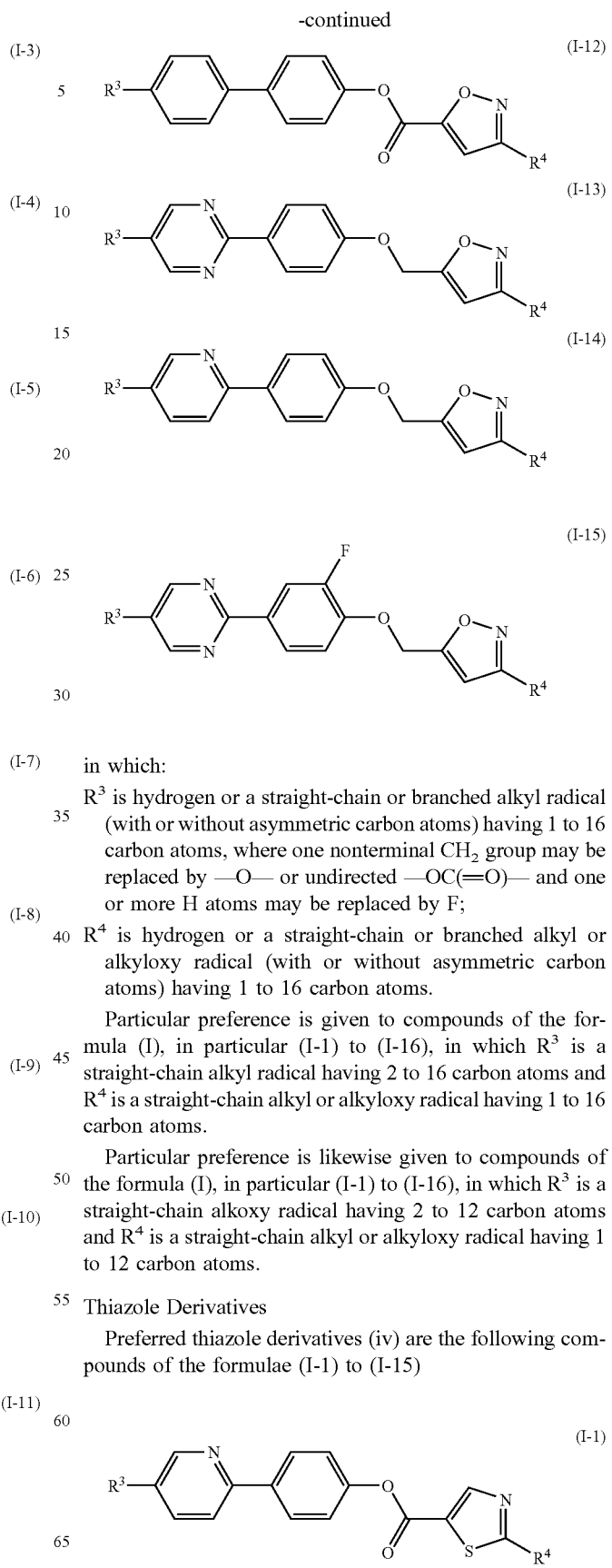

in which:

R³ is hydrogen or a straight-chain or branched alkyl radical (with or without asymmetric carbon atoms) having 1 to 16 carbon atoms, where one nonterminal CH₂ group may be replaced by —O— or undirected —OC(=O)— and one or more H atoms may be replaced by F;

R⁴ is hydrogen or a straight-chain or branched alkyl or alkyloxy radical (with or without asymmetric carbon atoms) having 1 to 16 carbon atoms.

Particular preference is given to compounds of the formula (I), in particular (I-1) to (I-16), in which R³ is a straight-chain alkyl radical having 2 to 16 carbon atoms and R⁴ is a straight-chain alkyl or alkyloxy radical having 1 to 16 carbon atoms.

Particular preference is likewise given to compounds of the formula (I), in particular (I-1) to (I-16), in which R³ is a straight-chain alkoxy radical having 2 to 12 carbon atoms and R⁴ is a straight-chain alkyl or alkyloxy radical having 1 to 12 carbon atoms.

Thiazole Derivatives

Preferred thiazole derivatives (iv) are the following compounds of the formulae (I-1) to (I-15)

-continued

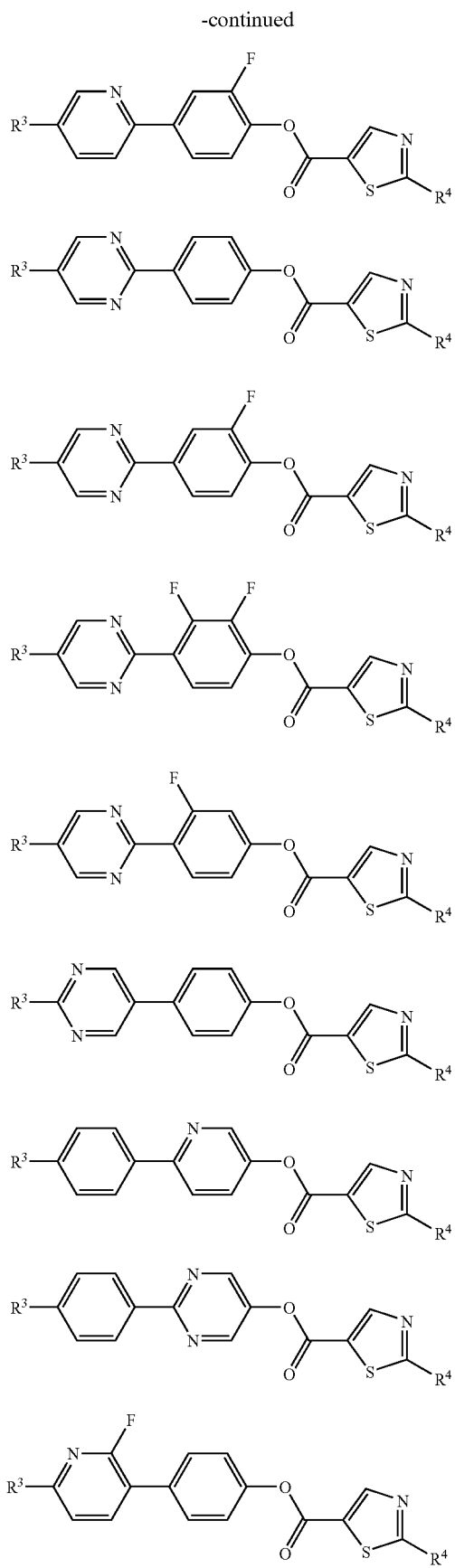
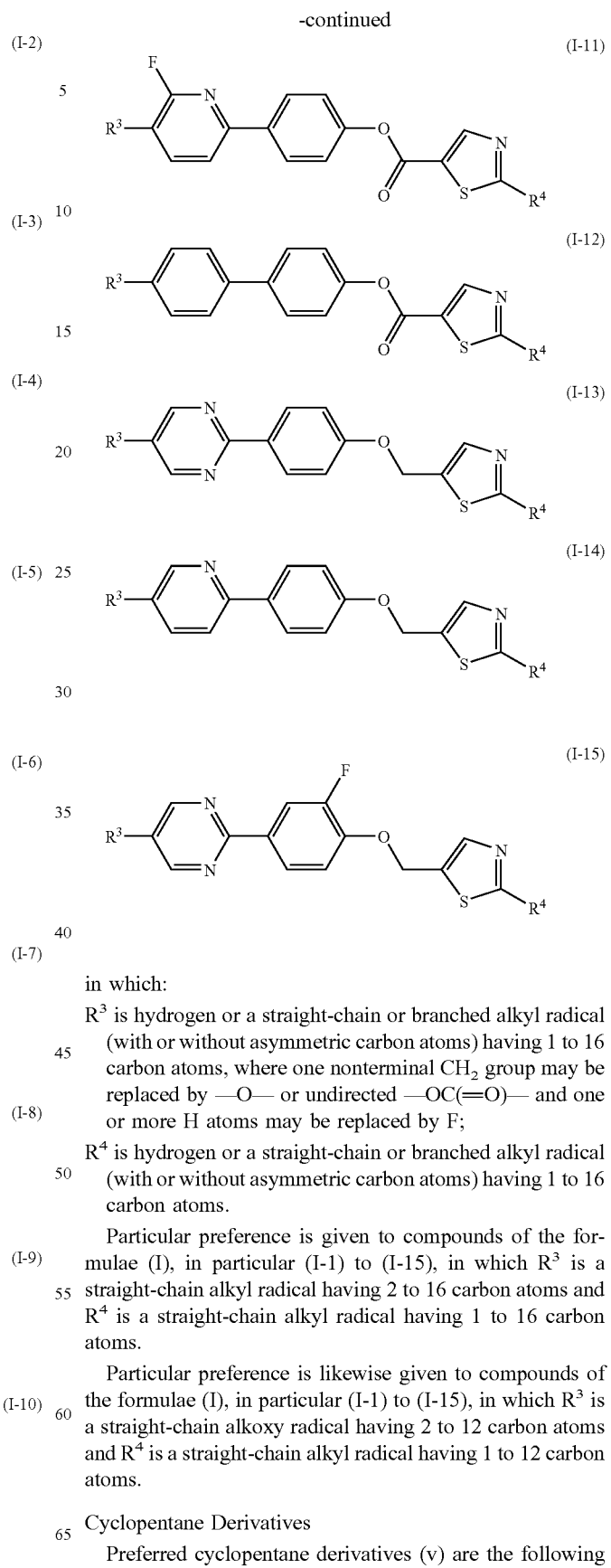

in which:

R³ is hydrogen or a straight-chain or branched alkyl radical (with or without asymmetric carbon atoms) having 1 to 16 carbon atoms, where one nonterminal CH₂ group may be replaced by —O— or undirected —OC(═O)— and one or more H atoms may be replaced by F;

R⁴ is hydrogen or a straight-chain or branched alkyl radical (with or without asymmetric carbon atoms) having 1 to 16 carbon atoms.

Particular preference is given to compounds of the formulae (I), in particular (I-1) to (I-15), in which R³ is a straight-chain alkyl radical having 2 to 16 carbon atoms and R⁴ is a straight-chain alkyl radical having 1 to 16 carbon atoms.

Particular preference is likewise given to compounds of the formulae (I), in particular (I-1) to (I-15), in which R³ is a straight-chain alkoxy radical having 2 to 12 carbon atoms and R⁴ is a straight-chain alkyl radical having 1 to 12 carbon atoms.

Cyclopentane Derivatives

Preferred cyclopentane derivatives (v) are the following compounds of the formulae (I-1) to (I-16)

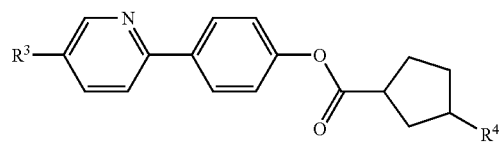 (I-1)

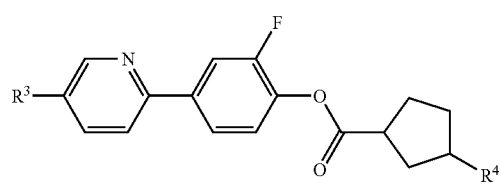 (I-2)

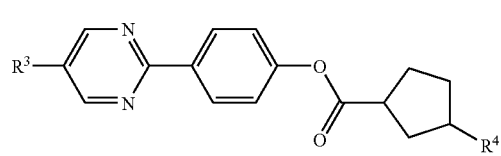 (I-3)

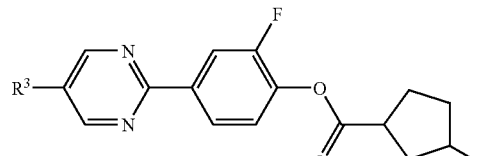 (I-4)

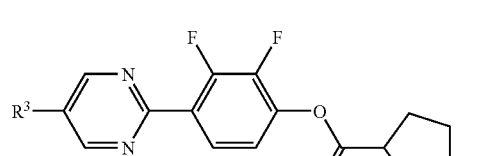 (I-5)

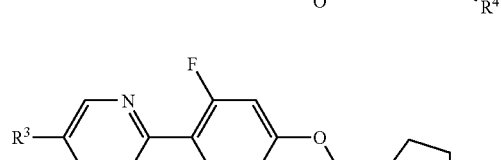 (I-6)

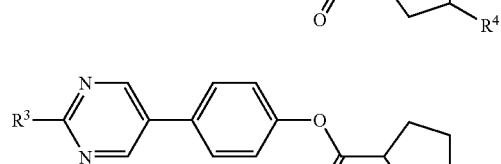 (I-7)

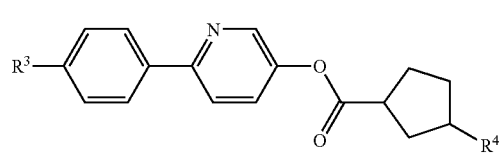 (I-8)

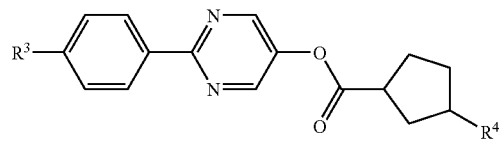 (I-9)

-continued

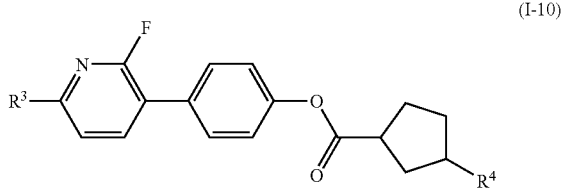 (I-10)

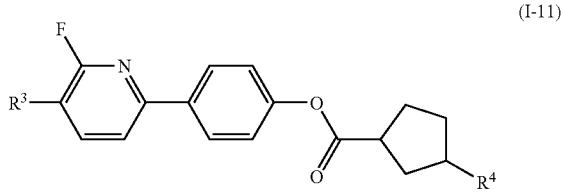 (I-11)

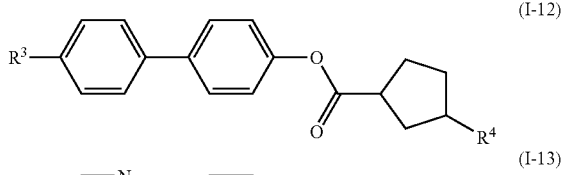 (I-12)

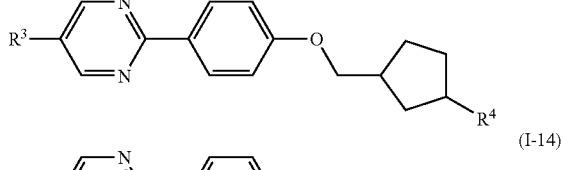 (I-13)

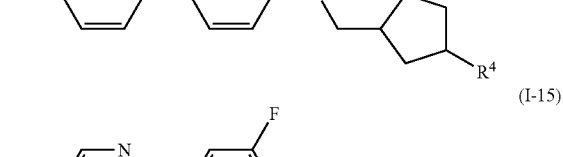 (I-14)

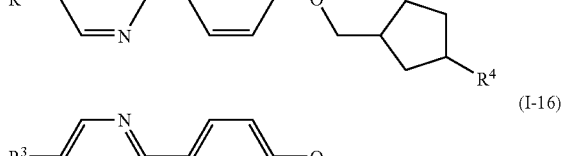 (I-15)

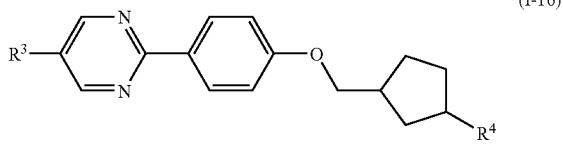 (I-16)

in which:

$R^3$ is hydrogen or a straight-chain or branched alkyl radical (with or without asymmetric carbon atoms) having 1 to 16 carbon atoms, where one nonterminal $CH_2$ group may be replaced by —O— or undirected —OC(=O)— and one or more H atoms may be replaced by F;

$R^4$ is hydrogen or a straight-chain or branched alkyl radical (with or without asymmetric carbon atoms) having 1 to 16 carbon atoms.

Particular preference is given to compounds of the formulae (I), in particular (I-1) to (I-16), in which $R^3$ and $R^4$ are each, independently of one another, a straight-chain alkyl radical having 2 to 16 carbon atoms.

Particular preference is likewise given to compounds of the formula (I), in particular (I-1) to (I-16), in which $R^3$ is a straight-chain alkoxy radical having 2 to 12 carbon atoms and $R^4$ is hydrogen or a straight-chain alkyl radical having 2 to 12 carbon atoms.

Cyclopentene Derivatives
T is preferably 1-cyclopentene-1,3-diyl, 1-cyclopentene-1,4-diyl or 3-cyclopentene-1,3-diyl.
Preferred cyclopentene derivatives (vi) are the following compounds of the formulae (I-1) to (I-45)
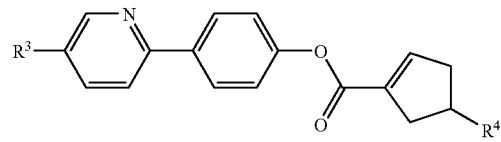
(I-1)
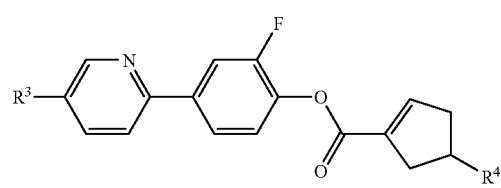
(I-2)
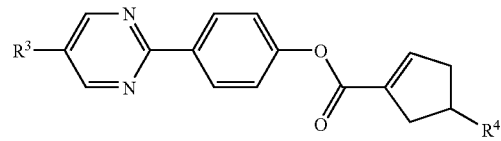
(I-3)
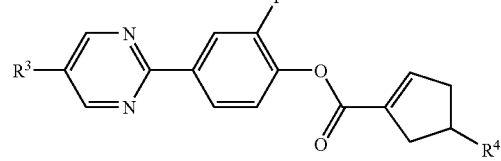
(I-4)
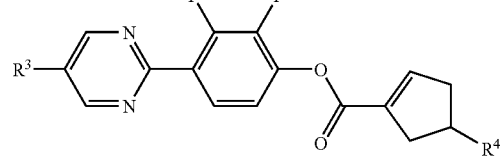
(I-5)
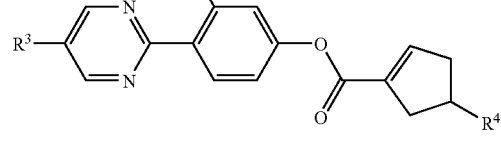
(I-6)
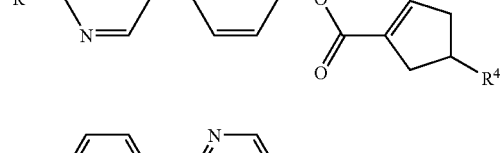
(I-7)
(I-8)
-continued
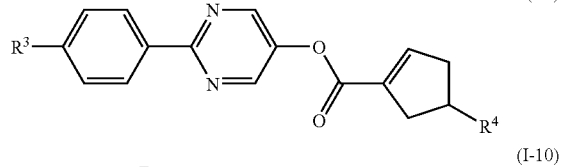
(I-9)
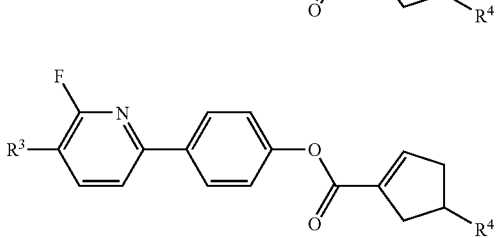
(I-10)
(I-11)
(I-12)
(I-13)
(I-14)
(I-15)
(I-16)
(I-17)

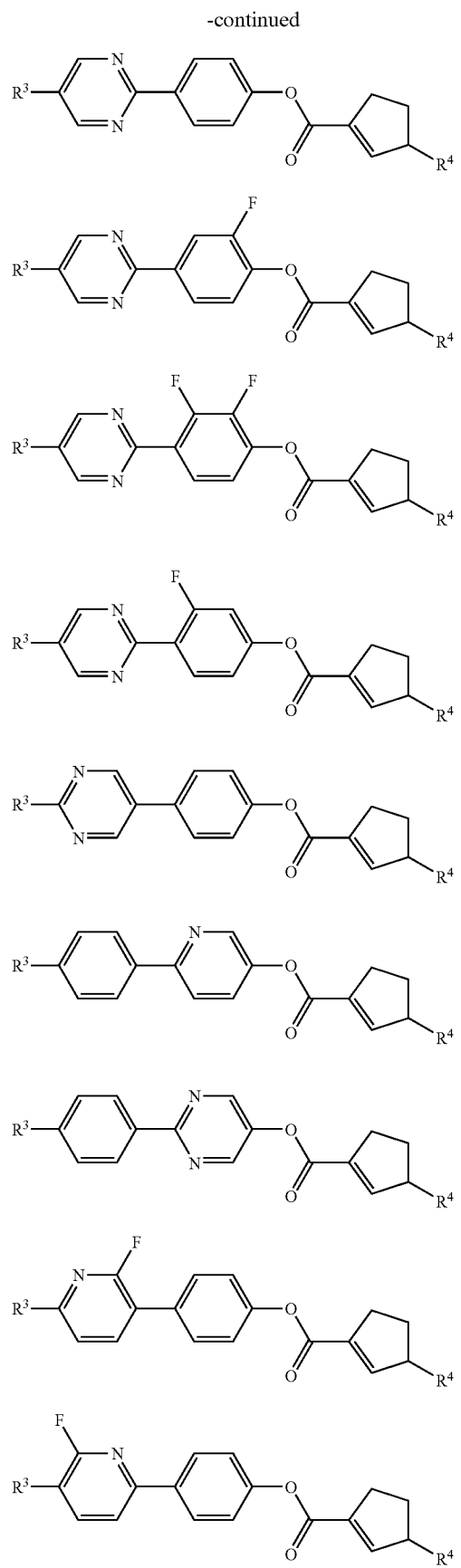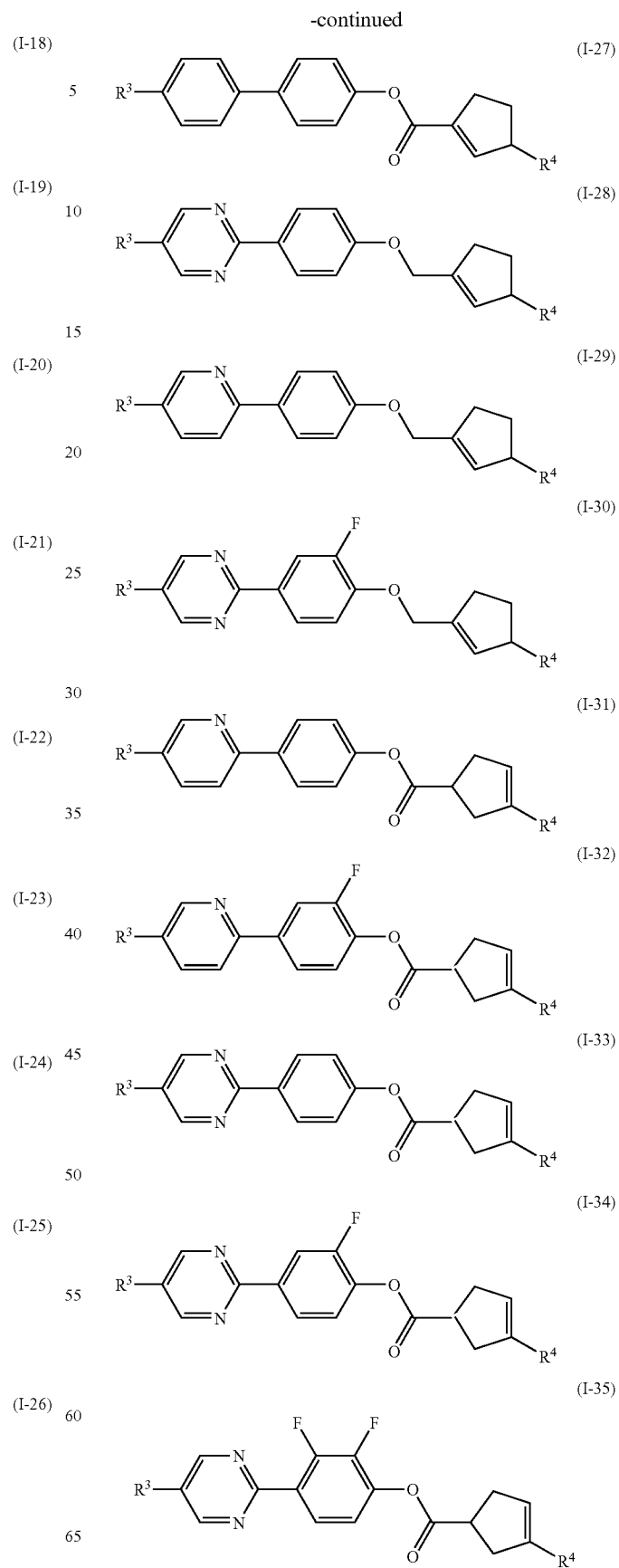

(I-36) 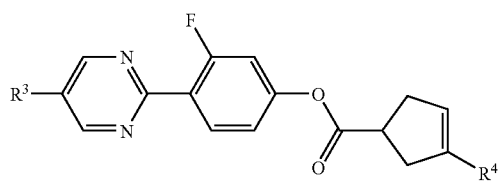

(I-37) 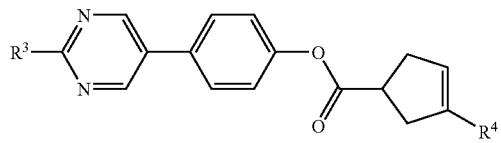

(I-38) 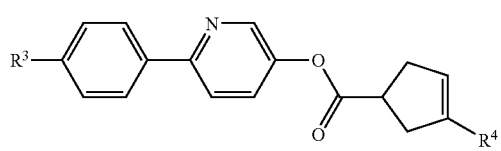

(I-39) 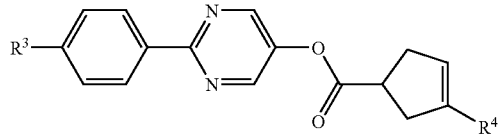

(I-40) 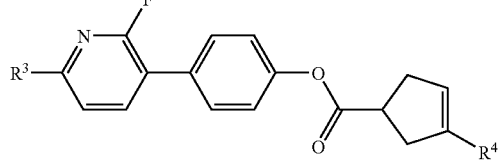

(I-41) 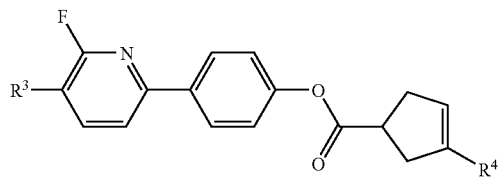

(I-42) 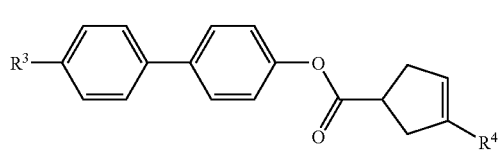

(I-43) 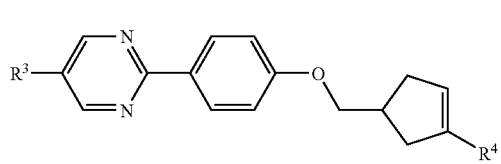

(I-44) 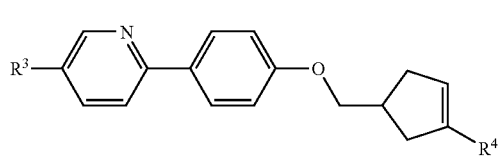

(I-45) 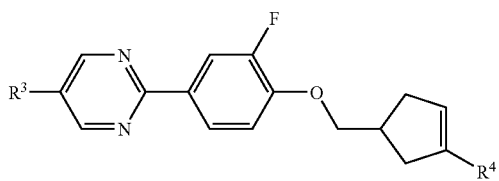

in which:

$R^3$ is hydrogen or a straight-chain or branched alkyl radical (with or without asymmetric carbon atoms) having 1 to 16 carbon atoms, where one nonterminal $CH_2$ group may, in addition, be replaced by —O— or, undirected, by —OC(=O)— and one or more H atoms may be replaced by F;

$R^4$ is hydrogen or a straight-chain or branched alkyl radical (with or without asymmetric carbon atoms) having 1 to 16 carbon atoms.

Particular preference is given to compounds of the formulae (I), in particular (I-1) to (I-45), in which $R^3$ and $R^4$ are each, independently of one another, a straight-chain alkyl radical having 1 to 16 carbon atoms.

Particular preference is likewise given to compounds of the formula (I), in particular (I-1) to (I-45), in which $R^3$ is a straight-chain alkoxy radical having 2 to 12 carbon atoms and $R^4$ is hydrogen or a straight-chain alkyl radical having 1 to 12 carbon atoms.

Particular preference is likewise given to compounds of the formula (I), in particular (I-1) to (I-45), in which $R^3$ is a branched alkyl or alkyloxy radical having 2 to 12 carbon atoms and $R^4$ is hydrogen or a straight-chain alkyl radical having 1 to 12 carbon atoms.

Of the compounds of the formula (I) which are to be used as optically active components (dopants) in liquid-crystal mixtures, preference is given to those in which the alkyl group contains the asymmetric carbon atoms in the form of at least one of the following groups:

a) —C*H(CH$_3$)C$_m$H$_{2m+1}$, where m has a value of from 2 to 8 b) —OC*H(CH$_3$)C$_m$H$_{2m+1}$, where m has a value of from 2 to 8 c) —OC*H(CH$_3$)CO$_2$ C$_m$H$_{2m+1}$, where m has a value of from 1 to 10 d) —OC(=O)C*H(CH$_3$)OC$_m$H$_{2m+1}$, where m has a value of from 1 to 10 e) —OC(=O)C*H(F)C$_m$H$_{2m+1}$, where m has a value of from 1 to 10 f) —OCH$_2$C*H(F)C$_m$H$_{2m+1}$, where m has a value of from 1 to 10 g) —OCH$_2$C*H(F)C*H(F)C$_m$H$_{2m+1}$, where m has a value of from 1 to 10 h) oxirane-2,3-diyl in which C* denotes the asymmetric carbon atom.

The compounds according to the invention are prepared by methods known per se from the literature, as described in standard works on organic synthesis, for example Houben-Weyl, Methoden der organischen Chemie [Methods of Organic Chemistry], Georg-Thieme-Verlag, Stuttgart.

However, it may prove necessary to vary or modify the literature methods for the requirements of mesogenic units, since, for example, functional derivatives having long (>$C_6$) alkyl chains tend to be less reactive than, for example, the methyl or ethyl analogues.

Particular reference is made in this connection to the following synthesis schemes for thiophene derivatives (i), in which the synthesis of the thiophene derivatives of the invention is illustrated in more detail by way of example.

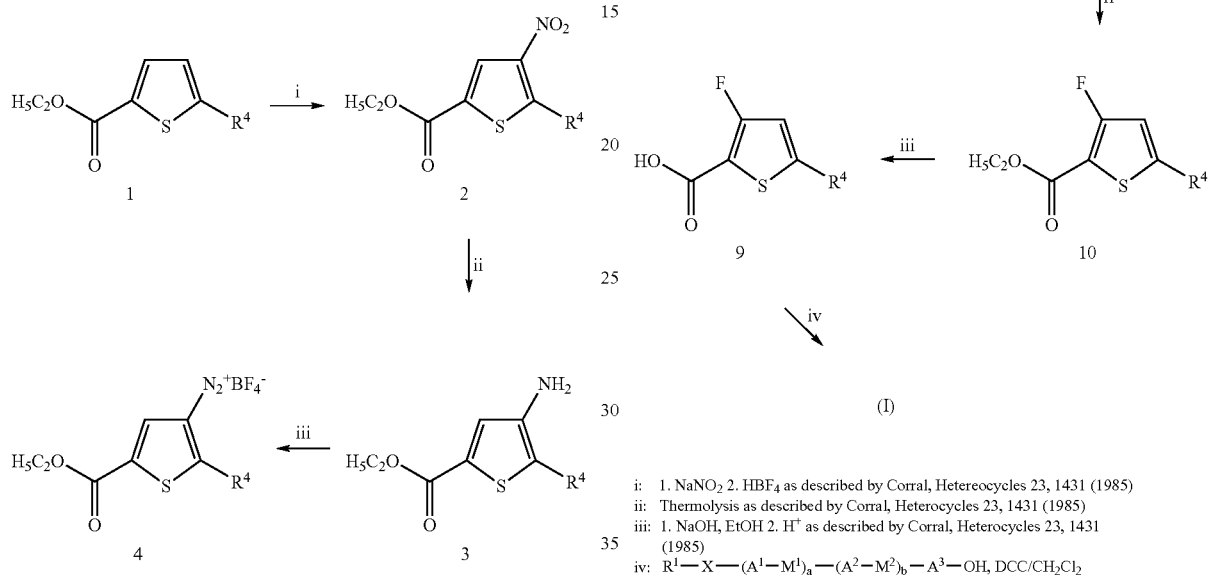

i: $HNO_3$, $H_2SO_4$ as described by Campaigne, J.Am.Chem.Soc. 73, 3812 (1951).
ii: Sn, HCl as described by Dewar, J.Am.Chem. 84, 3782 (1962)
iii: 1. $NaNO_2$ 2. $HBF_4$ as described by Corral, Heterocycles 23, 1431 (1985)
iv: Thermolysis as described by Corral, Heterocycles 23, 1431 (1985)
v: 1. NaOH, EtOH 2. $H^+$ as described by Corral, Heterocycles 23, 1431 (1985)
vi: $R^1$—X—$(A^1-M^1)_a$—$(A^2-M^2)_b$—$A^3$—OH, DCC/$CH_2Cl_2$ The 5-alkylthiophene-2-carboxylic esters 1 required for the synthesis in accordance with Scheme 1 are prepared as described in EP-B 0 500 072.

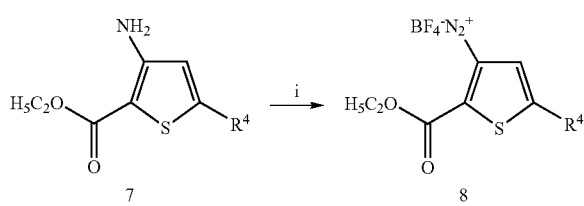

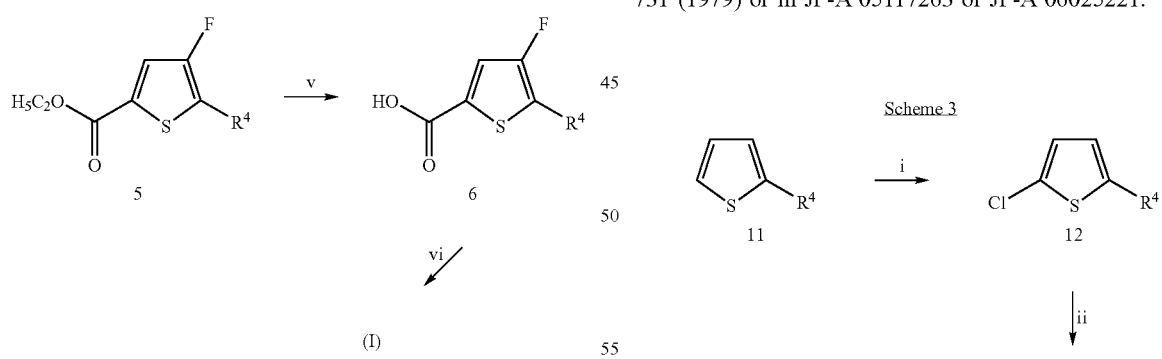

i: 1. $NaNO_2$ 2. $HBF_4$ as described by Corral, Hetereocycles 23, 1431 (1985)
ii: Thermolysis as described by Corral, Heterocycles 23, 1431 (1985)
iii: 1. NaOH, EtOH 2. $H^+$ as described by Corral, Heterocycles 23, 1431 (1985)
iv: $R^1$—X—$(A^1-M^1)_a$—$(A^2-M^2)_b$—$A^3$—OH, DCC/$CH_2Cl_2$ The 5-alkyl-3-amino-thiophene-2-carboxylic esters 7 required for the synthesis in accordance with Scheme 2 are prepared as described by Huddleston, Synth. Commun. 9, 731 (1979) or in JP-A 05117263 or JP-A 06025221.

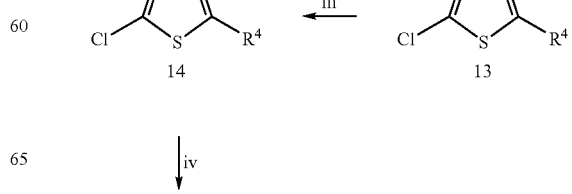

-continued

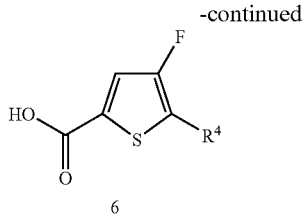

6

↓ v (I)

i: N-chlorosuccinimide, HOAc, benzene as described by Lucas, Tetrahedron Lett. 40, 1775 (1999)
ii: Br$_2$, CHCl$_3$ as described by Lucas, Tetrahedron Lett. 40, 1775 (1999)
iii: 1. BuLi 2. F-TEDA-BF$_4$; step 1 as described by Lucas, Tetrahedron Lett. 40, 1775 (1999)
iv: 1. BuLi 2. CO$_2$ as described by Lucas, Tetrahedron Lett. 40, 1775 (1999)
v: R$^1$—X—(A$^1$—M$^1$)$_a$—(A$^2$—M$^2$)$_b$—A$^3$—OH, DCC/CH$_2$Cl$_2$ The invention furthermore provides the intermediate 5-alkyl-4-fluoro-thiophene-2-carboxylic acids of the formula (II)

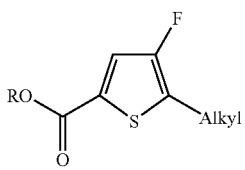
(II)

in which alkyl is a straight-chain or branched alkyl radical of 2 to 16 carbon atoms and R is hydrogen, alkali metal, alkaline earth metal (1/2), a straight-chain or branched alkyl radical of 1 to 16 atoms with the exception of methyl and tertbutyl, and 5-alkyl-3-fluoro-thiophene-2-carboxylic acids of the formula (III)

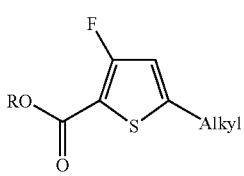
(III)

in which alkyl is a straight-chain or branched alkyl radical of 2 to 16 carbon atoms and R is hydrogen, alkali metal, alkaline earth metal (1/2), a straight-chain or branched alkyl radical of 1 to 16 atoms and corresponding acid halides, in particular acid chlorides, thereof.

Some of them correspond to the abovementioned compounds of the formulae 5, 6, 9 and 10. They can be used for preparing liquid crystals, agrochemicals and pharmaceuticals.

The 2-alkylthiophenes 11 required for the synthesis in accordance with Scheme 3 can be obtained as described in EP-B 0 500 072.

In this context, in particular for cyclopentane derivatives, reference is made to the synthesis schemes below in which the synthesis of the cyclopentane derivatives according to the invention is illustrated in more detail by way of example.

Scheme 1

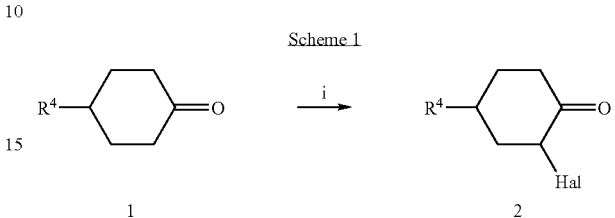

i: N-bromosuccinimide, CCl$_4$ as described by Corey, J.Am.Chem.Soc. 75, 2301 (1953).
ii: NaOCH$_3$, tert-butyl methyl ether as decribed in Organic Syntheses, Coll. Vol. IV, 594
iii: 1. NaOH/H$_2$O 2. HCl
iv: R$^1$—X—(A$^1$—M$^1$)$_a$—(A$^2$—M$^2$)$_b$—A$^3$—OH, DCC/CH$_2$Cl$_2$ If desired, this sequence may include an isomerization step to form the trans compounds, for example as described in U.S. Pat. No. 4,873,019 (Example 3), at an appropriate point (for example using 4).

In this context, in particular for cyclopentene derivatives, reference is made to the synthesis schemes below in which the synthesis of the cyclopentene derivatives according to the invention is illustrated in more detail by way of example.

Scheme 1

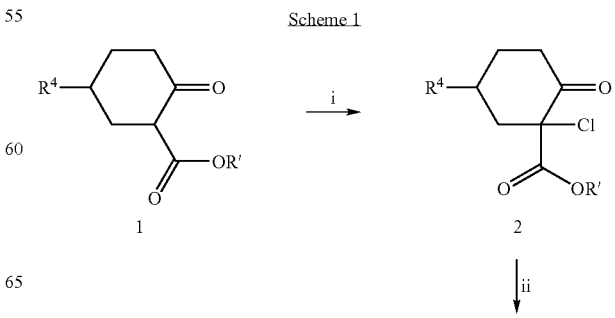

-continued

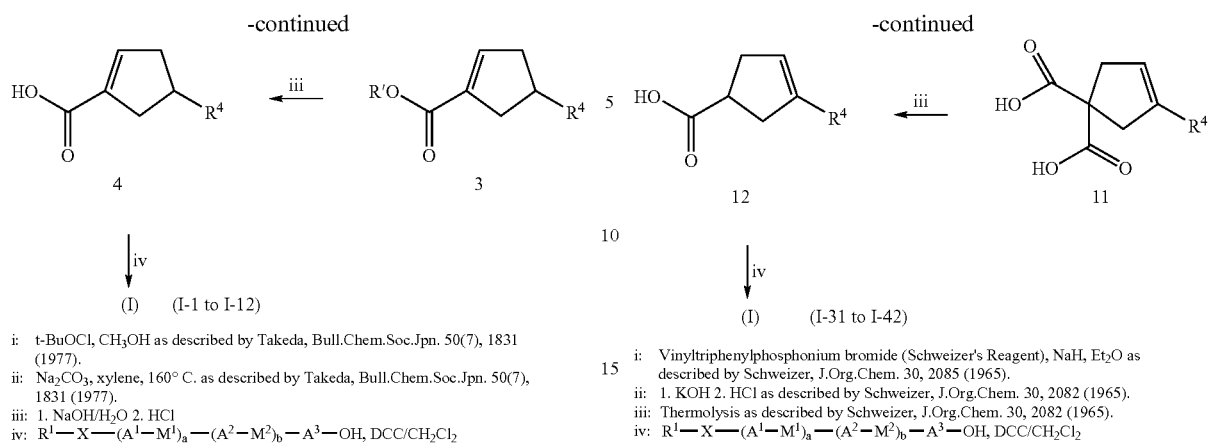

i: t-BuOCl, CH₃OH as described by Takeda, Bull.Chem.Soc.Jpn. 50(7), 1831 (1977).
ii: Na₂CO₃, xylene, 160° C. as described by Takeda, Bull.Chem.Soc.Jpn. 50(7), 1831 (1977).
iii: 1. NaOH/H₂O 2. HCl
iv: $R^1-X-(A^1-M^1)_a-(A^2-M^2)_b-A^3-OH$, DCC/CH₂Cl₂ i: Vinyltriphenylphosphonium bromide (Schweizer's Reagent), NaH, Et₂O as described by Schweizer, J.Org.Chem. 30, 2085 (1965).
ii: 1. KOH 2. HCl as described by Schweizer, J.Org.Chem. 30, 2082 (1965).
iii: Thermolysis as described by Schweizer, J.Org.Chem. 30, 2082 (1965).
iv: $R^1-X-(A^1-M^1)_a-(A^2-M^2)_b-A^3-OH$, DCC/CH₂Cl₂

The starting materials 9 required for the synthesis in accordance with Scheme 3 can be prepared as described by Hurd et al., J. Am. Chem. Soc. 70, 1650 (1948).

As far as the linking of functional derivatives of the furans, isoxazoles, thiazoles, cyclopentanes, cyclopentenes and fluorinated thiophenes with other liquid-crystal-specific units is concerned, express reference is made to DE-A 197 48 432, which gives a list of methods customary to the person skilled in the art.

The invention furthermore provides the use of compounds of the formula (I) in liquid-crystal mixtures, preferably smectic and nematic liquid-crystal mixtures, particularly preferably chiral smectic (ferroelectric) liquid-crystal mixtures. Particular preference is given to the use in ferroelectric liquid-crystal mixtures operated in inverse mode or in displays comprising active matrix elements. Very particular preference is given to the use in mixtures for active matrix LCDs in which the chiral smectic liquid-crystal layer forms a monostable monodomain.

The invention furthermore provides liquid-crystal mixtures, preferably smectic and nematic liquid-crystal mixtures, particularly preferably ferroelectric (chiral smectic) liquid-crystal mixtures, which comprise one or more compounds of the formula (I).

The liquid-crystal mixtures according to the invention generally comprise from 2 to 35 components, preferably from 2 to 25 components, particularly preferably from 2 to 20 components.

They generally comprise from 0.01 to 80% by weight, preferably from 0.1 to 60% by weight, particularly preferably from 0.1 to 30% by weight, based on the entire mixture, of one or more, preferably from 1 to 10, particularly preferably from 1 to 5, very particularly preferably from 1 to 3, compounds of the formula (I) according to the invention.

Scheme 2

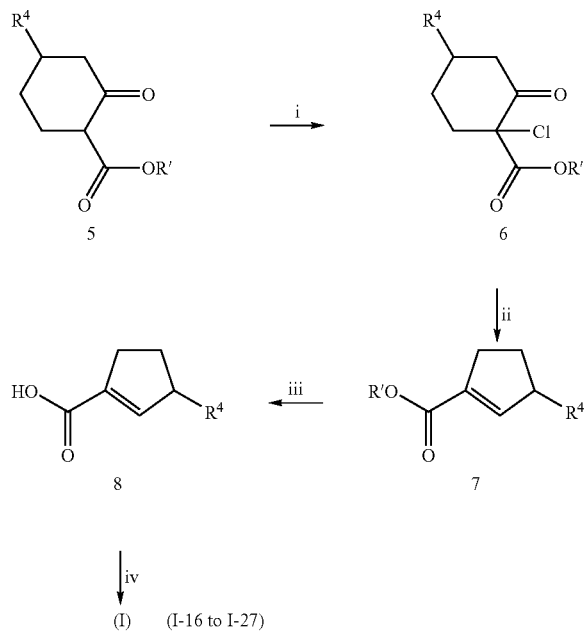

i: t-BuOCl, CH₃OH as described by Takeda, Bull.Chem.Soc.Jpn. 50(7), 1831 (1977).
ii: Na₂CO₃, xylene, 160° C. as described by Takeda, Bull.Chem.Soc.Jpn. 50(7), 1831 (1977).
iii: 1. NaOH/H₂O 2. HCl
iv: $R^1-X-(A^1-M^1)_a-(A^2-M^2)_b-A^3-OH$, DCC/CH₂Cl₂

The starting materials 1 and 5 required for the syntheses in accordance with schemes 1 and 2, respectively, can be prepared as described by Eisenbraun et al., J. Org. Chem. 32, 3010 (1967).

Further components of liquid-crystal mixtures which comprise compounds of the formula (I) according to the invention are preferably selected from known compounds having smectic and/or nematic and/or cholesteric phases. Further mixture components which are suitable in this context are listed, in particular, in international patent application PCT/EP96/03154 and in DE-A 197 48 432, which are incorporated herein by reference.

Scheme 3

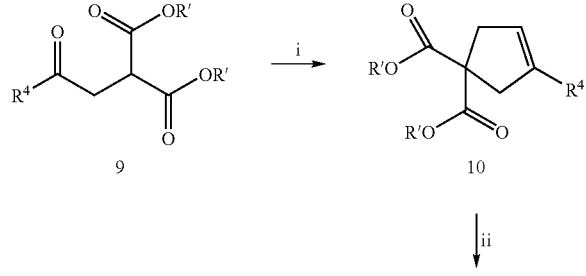

The mixtures according to the invention can in turn be used in electro-optical or fully optical elements, for example display elements, switching elements, light modulators, elements for image processing and/or signal processing, or generally in the area of nonlinear optics.

The invention therefore furthermore provides a switching and/or display device containing a liquid-crystal mixture, preferably a smectic liquid-crystal mixture, which comprises one or more compounds of the formula (I).

Particular preference is given to ferroelectric switching and/or display devices comprising active matrix elements (cf. e.g. DE-A 198 22 830).

The present application cites various documents, for example in order to illustrate the technical background to the invention. All these documents are incorporated herein by reference.

The examples which follow illustrate the invention.

Thiophene Derivatives

EXAMPLE 1

4-(5-Undecyl-pyrimidin-2-yl)phenyl 4-fluoro-5-propyl-thiophene-2-carboxylate 4.9 g of 4-(5-undecyl-pyrimidin-2-yl)phenol, 2.0 g of 4-fluoro-5-propyl-thiophene-2-carboxylic acid (prepared in accordance with Scheme 1 by nitrating methyl 5-propyl-thiophene-2-carboxylate in $HNO_3/H_2SO_4$ to form methyl 4-nitro-5-propyl-thiophene-2-carboxylate, followed by reduction of the latter by means of Sn/HCl to give the corresponding amino compound, conversion of the latter into the diazonium tetrafluoroborate, thermolysis and, finally, hydrolysis) and 2.1 g of dicyclohexylcarbodiimide are stirred for 24 h in 50 ml of dichloromethane at room temperature. Filtration, removal of the dichloromethane by distillation, purification by chromatography (silica gel; dichloromethane/heptane) and recrystallization from acetonitrile affords the target compound as colorless crystals.

The compounds (I-1) to (I-12) can be obtained in a similar manner, and the compounds (I-17) to (I-29) can be obtained in a similar manner using the 5-alkyl-3-fluoro-thiophene-2-carboxylic acids prepared in accordance with Scheme 2.

EXAMPLE 2

(4-Fluoro-5-propyl-thiophen-2-yl)methyl 4-(5-undecyl-pyrimidin-2-yl)phenyl ether A fully reacted mixture of equimolar amounts of diethyl azodicarboxylate and triphenylphosphine in THF is admixed with equimolar amounts of 4-(5-undecyl-pyrimidin-2-yl)phenol and 4-fluoro-5-propyl-thiophen-2-yl-methanol (prepared by $LiAlH_4$ reduction of methyl 4-fluoro-5-propyl-thiophene-2-carboxylate). After 24 h at room temperature the mixture is evaporated to dryness under reduced pressure. Purification by chromatography (silica gel, dichloromethane) and recrystallization affords the target compound.

The compounds (I-13) to (I-15) and (I-30) to (I-32) can be obtained in a similar manner.

The compounds of the formulae (I-16) and (I-33) can be obtained via the sequence 4-(or 3-)fluoro-5-alkyl-thiophen-2-yl-methanol-2-bromomethyl-4-(or 3-) fluoro-5-alkyl-thiophene-2-bromomethyl-5-alkyl-4-(or 3-)fluoro-thiophen-2-yl-triphenylphosphonium salt—Wittig reaction with 4-(5-$R^3$-pyrimidin-2-yl)benzaldehyde-hydrogenation.

Furan Derivatives

EXAMPLE 1

4-(5-Undecyl-pyrimidin-2-yl)phenyl 5-ethyl-furan-2-carboxylate 4.9 g of 4-(5-undecyl-pyrimidin-2-yl)phenol, 1.4 g of 5-ethyl-2-furancarboxylic acid (prepared as described by Perry et al., Appl. Organomet. Chem. 10, 389–392 (1996) from furan-2-carboxylic acid; m.p. 90° C.) and 2.1 g of dicyclohexylcarbodiimide are stirred for 24 h in 50 ml of dichloromethane at room temperature. Filtration, removal of the dichloromethane by distillation, purification by chromatography (silica gel; dichloromethane/heptane) and recrystallization from acetonitrile affords the target compound as colorless crystals having the phase sequence X 80 (N62) I.

The following compound is prepared in a similar manner.

EXAMPLE 2

2-Fluoro-4-(5-undecyl-pyridin-2-yl)phenyl 5-ethyl-furan-2-carboxylate which has a melting point of 76° C.

The compounds (1-1) to (1-12) can be prepared similarly to Example 1.

EXAMPLE 3

(5-Ethyl-furan-2-yl)methyl 4-(5-undecyl-pyrimidin-2-yl)phenyl ether

A fully reacted mixture of equimolar amounts of diethyl azodicarboxylate and triphenylphosphine in THF is admixed with equimolar amounts of 4.9 g of 4-(5-undecyl-pyrimidin-2-yl)phenol and 5-ethyl-furan-2-yl-methanol (prepared by $LiAlH_4$ reduction of methyl 5-ethyl-furan-2-carboxylate, which in turn can be obtained by esterification of 5-ethyl-furan-2-carboxylic acid from Example 1). The mixture is stirred for 24 h at room temperature and then evaporated to dryness under reduced pressure. Purification by chromatography (silica gel, dichloromethane) and recrystallization affords the target compound.

The compounds (I-13) to (I-15) can be obtained in a similar manner.

The compounds of the formula (I-16) can be obtained via the sequence 5-ethyl-furan-2-yl-methanol— 2-bromomethyl-5-ethyl-furan— 2-bromomethyl-5-ethyl-furan-triphenylphosphonium salt— Wittig reaction with 4-(5-$R^3$-pyrimidin-2-yl)benzaldehyde— hydrogenation.

The following compounds were obained in a similar manner:

EXAMPLE 4

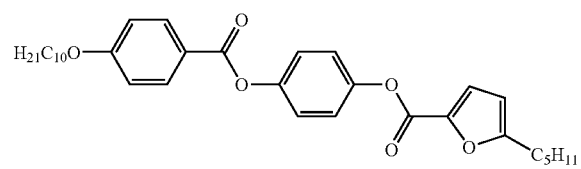

X 95 (N 92) I 4-(4-Decyloxy-benzoyloxy)phenyl 5-pentylfuran-2-carboxylate

EXAMPLE 5

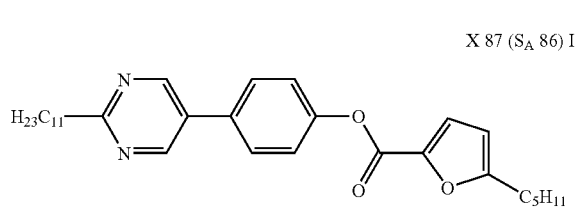

4-(2-Undecyl-pyrimidin-5-yl)phenyl 5-pentylfuran-2-carboxylate

EXAMPLE 6

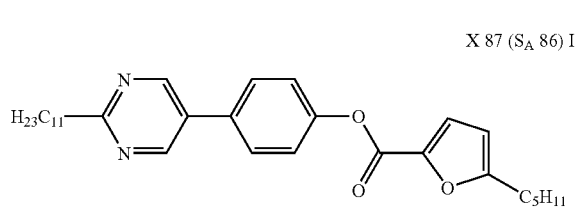

4-(5-Undecyl-pyrimidin-2-yl)phenyl 5-pentylfuran-2-carboxylate

EXAMPLE 7

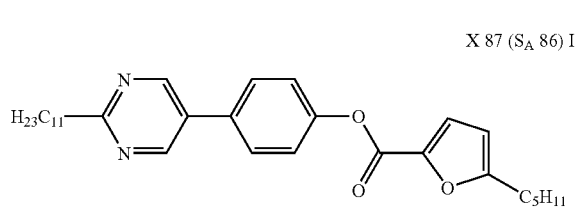

2-Fluoro-4-(5-undecyl-pyrimidin-2-yl)phenyl 5-pentylfuran-2-carboxylate

EXAMPLE 8

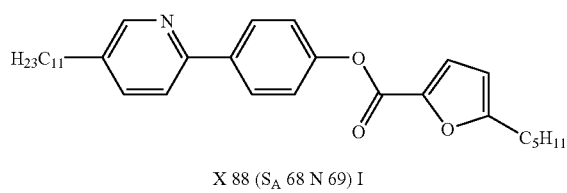

4-(5-Undecyl-pyridin-2-yl)phenyl 5-pentylfuran-2-carboxylate

EXAMPLE 9

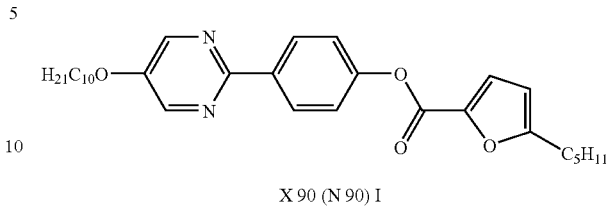

4-(5-Decyloxy-pyrimidin-2-yl)phenyl 5-pentylfuran-2-carboxylate

EXAMPLE 10

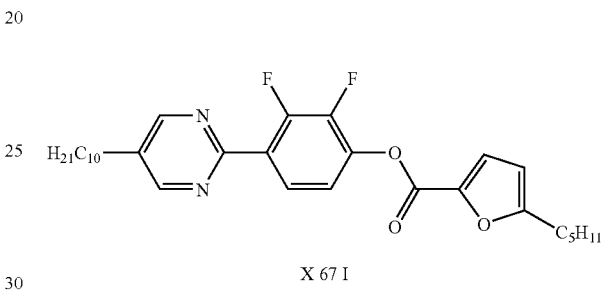

2,3-Difluoro-4-(5-decyl-pyrimidin-2-yl)phenyl 5-pentylfuran-2-carboxylate

EXAMPLE 11

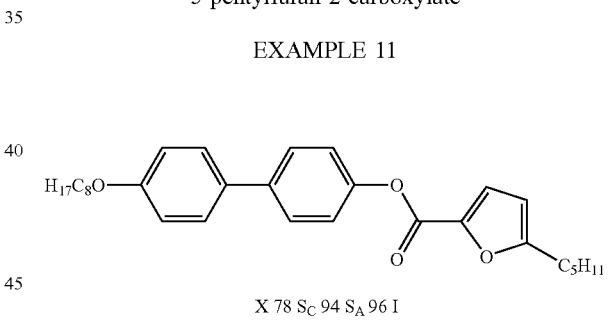

4-(4-Octyloxyphenyl)phenyl 5-pentylfuran-2-carboxylate

EXAMPLE 12

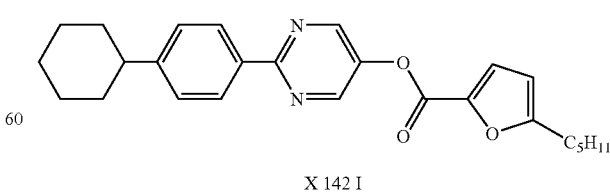

2-(4-Cyclohexylphenyl)pyrimidin-5-yl 5-pentylfuran-2-carboxylate

EXAMPLE 13

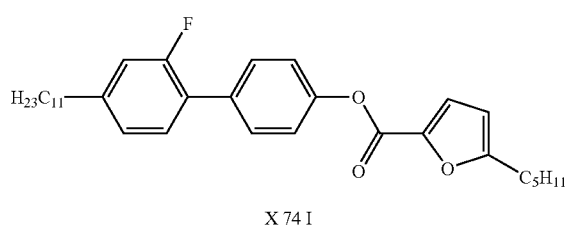

X 74 I 4-(2-Fluoro-4-undecyl-phenyl)phenyl 5-pentylfuran-2-carboxylate

Isoxazole Derivatives

EXAMPLE 1

4-(5-Undecyl-pyrimidin-2-yl)phenyl 3-propyloxy-isoxazole-5-carboxylate 4.9 g of 4-(5-undecyl-pyrimidin-2-yl)phenol, 1.7 g of 3-propyloxy-isoxazole-5-carboxylic acid (prepared as described by Xue et al., Bioorg. Med. Chem. Letters 8 (1998) 3499 by reacting methyl 3-hydroxy-isoxazole-5-carboxylate, which is commercially available, with 1-bromopropane at 60° C. in dimethylformamide/potassium carbonate followed by hydrolysis with LiOH in tetrahydrofuran) and 2.1 g of dicyclohexylcarbodiimide are stirred for 24 h in 50 ml of dichloromethane at room temperature. Filtration, removal of the dichloromethane by distillation, purification by chromatography (silica gel; dichloromethane/heptane) and recrystallization from acetonitrile affords the target compound as colorless crystals having the phase sequence X 91 $S_A$ 109 N 126 I.

The compounds (I-1) to (I-12) in which $R^4$ is an alkoxy radical can be prepared similarly to Example 1, and the compounds (I-1) to (I-12) in which $R^4$ is an alkyl radical can likewise be prepared using 3-alkyl-isoxazole-5-carboxylic acids prepared as described by Dulin et al., Proc.Soc.exp-.Biol.Med., 1966, 121, 777.

EXAMPLE 2

(3-Propyloxy-isoxazol-5-yl)methyl 4-(5-undecyl-pyrimidin-2-yl)phenyl ether

A fully reacted mixture of equimolar amounts of diethyl azodicarboxylate and triphenylphosphine in THF is admixed with equimolar amounts of 4-(5-undecyl-pyrimidin-2-yl) phenol and 3-propyloxy-isoxazol-5-yl-methanol (prepared by LiAlH$_4$ reduction of methyl 3-propyloxy-isoxazole-5-carboxylate). The mixture is stirred for 24 h at room temperature and then evaporated to dryness under reduced pressure. Purification by chromatography (silica gel, dichloromethane) and recrystallization affords the target compound.

The compounds (I-13) to (I-15) can be prepared in a similar manner.

Thiazole Derivatives

EXAMPLE 1

[4-(5-Undecyl-pyrimidin-2-yl)phenyl]2-propyl-thiazole-5-carboxylate 4.9 g of 4-(5-undecyl-pyrimidin-2-yl)phenol, 1.7 g of 2-propyl-thiazole-5-carboxylic acid (prepared as described by Clemence et al., Eur. J. Med. Chem. Chimica Therapeutica 1976-11, no. 6, p. 567–570) and 2.1 g of dicyclohexylcarbodiimide are stirred for 24 h in 50 ml of dichloromethane at room temperature. Filtration, removal of the dichloromethane by distillation, purification by chromatography (silica gel; dichloromethane/heptane) and recrystallization from acetonitrile affords the target compound as colorless crystals.

The compounds (I-1) to (I-12) can be prepared in a similar manner to Example 1.

EXAMPLE 2

(2-Propyl-thiazol-5-yl)methyl 4-(5-undecyl-pyrimidin-2-yl)phenyl ether

A fully reacted mixture of equimolar amounts of diethyl azodicarboxylate and triphenylphosphine in THF is admixed with equimolar amounts of 4-(5-undecyl-pyrimidin-2-yl) phenol and 2-propylthiazol-5-yl-methanol (prepared by LiAlH$_4$ reduction of methyl 2-propylthiazole-5-carboxylate). The mixture is stirred for 24 h at room temperature and then evaporated to dryness under reduced pressure. Purification by chromatography (silica gel, dichloromethane) and recrystallization affords the target compound.

The compounds (I-13) to (I-15) can be obtained in a similar manner.

Cyclopentane Derivatives

EXAMPLE 1

4-(5-Undecyl-pyrimidin-2-yl)phenyl 3-ethyl-cyclopentanecarboxylate 4.9 g of 4-(5-undecyl-pyrimidin-2-yl)phenol, 1.5 g of 3-ethyl-cyclopentanecarboxylic acid and 2.1 g of dicyclohexylcarbodiimide are stirred for 24 h in 50 ml of dichloromethane at room temperature. Filtration, removal of the dichloromethane by distillation, purification by chromatography (silica gel; dichloromethane/heptane) and recrystallization from acetonitrile affords the target compound as colorless crystals.

The compounds (I-1) to (I-12) can be obtained in a similar manner.

EXAMPLE 2

4-(5-Undecyl-pyrimidin-2-yl)phenyl (3-ethyl-cyclopentan-1-yl)methyl ether

A fully reacted mixture of equimolar amounts of diethyl azodicarboxylate and triphenylphosphine in THF is admixed with equimolar amounts of 4-(5-undecyl-pyrimidin- 2-yl) phenol and 3-ethyl-cyclopentan-1-yl-methanol (prepared by LiAlH$_4$ reduction of methyl 3-ethyl-cyclopentanecarboxylic acid). The mixture is stirred for 24 h at room temperature and then evaporated to dryness under reduced pressure. Purification by chromatography (silica gel, dichloromethane) and recrystallization affords the target compound.

The compounds (I-13) to (I-15) can be obtained in a similar manner.

The compounds of the formulae (I-16) and (I-33) can be obtained via the sequence
3-alkyl-cyclopentan-1-yl-methanol
1-bromomethyl-3-alkyl-cyclopentane
(1-bromomethyl-3-alkyl-cyclopentane)triphenylphosphonium salt
Wittig reaction with 4-(5-$R^3$-pyrimidin-2-yl)benzaldehyde
hydrogenation The following compounds were obtained in a similar manner:

EXAMPLE 3

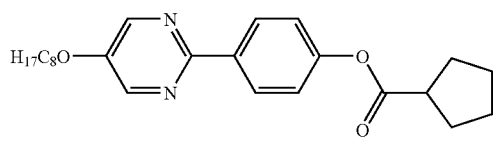

X 95 I 4-(5-Octyloxy-pyrimidin-2-yl)phenyl cyclopentanecarboxylate

EXAMPLE 4

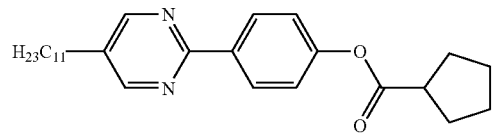

X 73 I 4-(5-Undecyl-pyrimidin-2-yl)phenyl cyclopentanecarboxylate

EXAMPLE 5

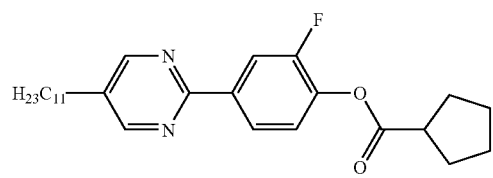

X 66 I

2-Fluoro-4-(5-undecyl-pyrimidin-2-yl)phenyl cyclopentanecarboxylate

EXAMPLE 6

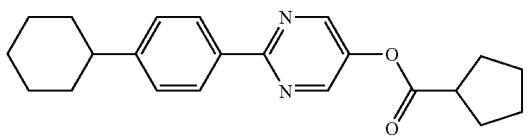

X 164 I 2-(4-Cyclohexyl)phenyl-pyrimidin-5-yl cyclopentanecarboxylate

Cyclopentene Derivatives

EXAMPLE 1

4-(5-Undecyl-pyrimidin-2-yl)phenyl 3-ethyl-1-cyclopentene-1-carboxylate 4.9 g of 4-(5-undecyl-pyrimidin-2-yl)phenol, 1.5 g of 3-ethyl-1-cyclopentene-1-carboxylic acid and 2.1 g of dicyclohexylcarbodiimide are stirred for 24 h in 50 ml of dichloromethane at room temperature. Filtration, removal of the dichloromethane by distillation, purification by chromatography (silica gel; dichloromethane/heptane) and recrystallization from acetonitrile affords the target compound.

The compounds (I-1) to (I-12), (I-16) to (I-27) and (I-31) to (I-42) can be obtained in a similar manner.

EXAMPLE 2

(3-Ethyl-1-cyclopenten-1-yl)methyl 4-(5-undecyl-pyrimidin-2-yl)phenyl ether

A fully reacted mixture of equimolar amounts of diethyl azodicarboxylate and triphenylphosphine in THF is admixed with equimolar amounts of 4-(5-undecylpyrimidin-2-yl)phenol and 3-ethyl-1-cyclopenten-1-yl-methanol (prepared by LiAlH$_4$ reduction of methyl 3-ethyl-1-cyclopentene-1-carboxylate as described by Takeda, Bull.Chem.Soc.Jpn. 50 (7), 1831 (1977)). The mixture is stirred for 24 h at room temperature and then evaporated to dryness under reduced pressure. Purification by chromatography (silica gel, dichloromethane) and recrystallization affords the target compound.

The compounds (I-13) to (I-15), (I-28) to (I-30) and (I-43) to (I-45) can be obtained in a similar manner.

The following compounds were obtained in a similar manner:

EXAMPLE 3

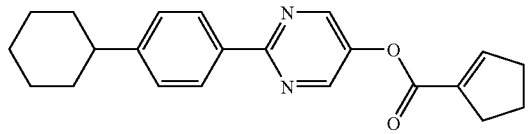

X 176 I 2-(4-Cyclohexyl)phenyl-pyrimidin-5-yl cyclopent-1-ene-1-carboxylate

EXAMPLE 4

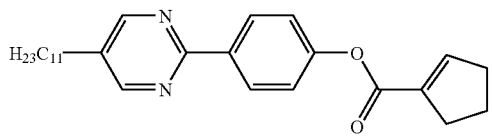

X 109 I 4-(5-Undecyl-pyrimidin-2-yl)phenyl cyclopent-1-ene-1-carboxylate

The invention claimed is:
1. A five-membered ring compound of the formula (I),

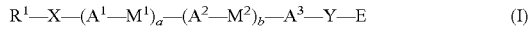

$$R^1-X-(A^1-M^1)_a-(A^2-M^2)_b-A^3-Y-E \qquad (I)$$

where the symbols and indices have the following meanings:

E is a radical T—Z—$R^2$ containing a five-membered ring, where:
(i) T is undirected and is 4-fluorothiophene-2,5-diyl, 3-fluorothiophene-2,5-diyl, 3-fluorothiophene-2,4-diyl or 5-fluorothiophene-2,4-diyl
  Z is a single bond or —O—
  $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, with the provisos that
    a) the —$CH_2$— group nearest to the thiophene cannot be replaced by —O— when Z is —O—
    b) $R^2$ can only be hydrogen when Z is a single bond,
  Y is —OC(=O)—, —$OCH_2$—, —$CH_2CH_2$—
  a, b are each, independently of one another, 0 or 1
(ii) T is furan-2,5-diyl or furan-2,4-diyl
  Z is a single bond or —O—
  $R^2$ is a straight-chain or branched alkyl radical (with or without asymmetric carbon atoms) having 1 to 20 carbon atoms, where one nonterminal $CH_2$ group nonadjacent to furan may be replaced by —O— or —OC(=O)— or —C(=O)O— and/or one or more H atoms may be replaced by F,
  Y is —OC(=O)—, —$OCH_2$—, —$CH_2CH_2$—
  a, b are each, independently of one another, 0 or 1

(iii) T is undirected and is isoxazole-3,5-diyl
  Z is a single bond or —O—
  $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, with the provisos that
    a) the —$CH_2$— group nearest to the isoxazole cannot be replaced by —O— when Z is —O—
    b) $R^2$ can only be hydrogen when Z is a single bond,
  a is 1
  b is 0 or 1
  Y is —OC(=O)—, —$OCH_2$—, —$CH_2CH_2$—
(iv) T is undirected and is of thiazole-2,4-diyl
  Z is a single bond
  $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F,
  Y is —OC(=O)—, —$OCH_2$—, —$CH_2CH_2$—
  a, b are each, independently of one another, 0 or 1
(v) T is cyclopentane-1,3-diyl, in which one —$CH_2CH_2$— or —$CH_2CH$— group is replaced by a —CH=CH— or CH=C— group respectively
  Z is a single bond
  $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)— and/or one or more H atoms may be replaced by F, with the proviso that the —$CH_2$— group nearest to the cyclopentene cannot be replaced and where
  a is 1
  b is 0 or 1
  Y is —OC(=O), —$OCH_2$—
$R^1$ is hydrogen or a straight-chain or branched $C_{1-20}$-alkyl or $C_{2-20}$-alkenyl radical (with or without asymmetric carbon atoms), where
  a) one or two nonterminal $CH_2$ groups may be replaced, independently of one another, by —O— or —C(=O)—, with the proviso that two adjacent $CH_2$ groups cannot be replaced in the same way, and/or
  b) one $CH_2$ group may be replaced by —C≡C—, and/or
  c) one $CH_2$ group may be replaced by —$Si(CH_3)_2$—, cyclopropane-1,2-diyl, cyclobutane-1,3-diyl, cyclopentane-1,4-diyl, bicyclo[1.1.1]pentane-1,3-diyl or cyclohexane-1,4-diyl, and/or
  d) one or more H atoms may be replaced by F and/or CN,
  e) in the case of a branched alkyl radical containing asymmetric carbon atoms, the asymmetric carbon atoms have —$CH_3$, —$OCH_3$, —$CF_3$, F, CN and/or Cl as substituents or are incorporated into a 3- to 7-membered ring, in which, in addition, one or two non-adjacent $CH_2$ groups may be replaced by —O— and one $CH_2$ group non-adjacent to these groups may be replaced by —OC(=O)—;
X is a single bond, —O—, OC(=O), —C(=O)O— or —OC(=O)O—;
$A^1$, $A^2$, $A^3$ are each, independently of one another, phenylene-1,4-diyl, unsubstituted or monosubstituted or disubstituted by CN or F, phenylene-1,3-diyl, unsubstituted or monosubstituted or disubstituted by CN or F, cyclohexane-1,4-diyl, in which one or two H atoms may be replaced by CN and/or $CH_3$ and/or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, cyclopentane-2,5-diyl or thiophene-2,5-diyl;

$M^1$, $M^2$ are undirected and are each, independently of one another, —OC(=O)—, —OCH$_2$—, —CH$_2$CH$_2$—, —OC(=O)CH$_2$CH$_2$—, —OCH$_2$CH$_2$CH$_2$—, —C=C—, —CH$_2$CH$_2$CH$_2$CH$_2$— or a single bond.

2. A liquid-crystal mixture comprising at least one compound of the formula (I) as claimed in claim 1.

3. A liquid-crystal mixture as claimed in claim 2, which comprises from 0.01 to 80% by weight, based on the entire weight of the mixture, of one or more compounds of the formula (I).

4. A liquid-crystal mixture as claimed in claim 2, which is ferroelectric (chiral smectic).

5. A liquid-crystal mixture as claimed in claim 2, which is nematic.

6. A ferroelectric switching and/or display device, which contains a ferroelectric liquid-crystal mixture as claimed in claim 4.

7. A ferroelectric switching and/or display device as claimed in claim 6, which contains active matrix elements and wherein the liquid-crystal layer forms a monostable monodomain.

8. A liquid-crystal mixture as claimed in claim 2, which comprises 0.1 to 30% by weight, based on the entire weight of the mixture, of one or more compounds of formula (I).

9. The liquid-crystal mixture of claim 8, which is ferroelectric (chiral smectic) and further comprises one or more compounds having a smectic phase.

10. The liquid-crystal mixture of claim 8, which is nematic and further comprises one or more compounds having a nematic phase.

11. The ferroelectric switching and/or display device of claim 7, which contains a liquid-crystal mixture comprising at least one compound of the formula (I):

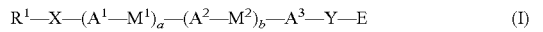

(I)

where the symbols and indices have the following meanings:

E is a radical T—Z—$R^2$ containing a five-membered ring, where:

(i) T is undirected and is 4-fluorothiophene-2,5-diyl, 3-fluorothiophene-2,5-diyl, 3-fluorothiophene-2,4-diyl or 5-fluorothiophene-2,4-diyl
Z is a single bond or —O—
$R^2$ is hydrogen or a straight-chain or branched alkyl radical (with or without asymmetric carbon atoms) having 1 to 20 carbon atoms, where one nonterminal CH$_2$ group may be replaced by —O— or —OC(=O)— or —C(=O)O— and/or one or more H atoms may be replaced by F, with the provisos that
a) the —CH$_2$— group nearest to the thiophene cannot be replaced by —O— when Z is —O—
b) $R^2$ can only be hydrogen when Z is a single bond,
Y is —OC(=O)—, —OCH$_2$—, —CH$_2$CH$_2$—
a, b are each, independently of one another, 0 or 1

(ii) T is furan-2,5-diyl or furan-2,4-diyl
Z is a single bond or —O—
$R^2$ is a straight-chain or branched alkyl radical (with or without asymmetric carbon atoms) having 1 to 20 carbon atoms, where one nonterminal CH$_2$ group nonadjacent to furan may be replaced by —O— or —OC(=O)— or —C(=O)O— and/or one or more H atoms may be replaced by F,
Y is —OC(—O)—, —OCH$_2$—, —CH$_2$CH$_2$—
a, b are each, independently of one another, 0 or 1

(iii) T is undirected and is isoxazole-3,5-diyl
Z is a single bond or —O—
$R^2$ is hydrogen or a straight-chain or branched alkyl radical (with or without asymmetric carbon atoms) having 1 to 20 carbon atoms, where one nonterminal CH$_2$ group may be replaced by —O— or —OC(=O)— or —C(=O)O— and/or one or more H atoms may be replaced by F, with the provisos that
a) the —CH$_2$— group nearest to the isoxazole cannot be replaced by —O— when Z is —O—
b) $R^2$ can only be hydrogen when Z is a single bond,
a is 1
b is 0 or 1
Y is —OC(=O)—, —OCH$_2$—, —CH$_2$CH$_2$—

(iv) T is undirected and is er thiazole-2,4-diyl
z is a single bond
$R^2$ is hydrogen or a straight-chain or branched alkyl radical (with or without asymmetric carbon atoms) having 1 to 20 carbon atoms, where one nonterminal CH$_2$ group may be replaced by —O— or —OC(=O)— or —C(=O)O— and/or one or more H atoms may be replaced by F,
Y is —OC(=O)—, —OCH$_2$—, —CH$_2$CH$_2$—
a, b are each, independently of one another, 0 or 1

(v) T is cyclopentane-1,3-diyl, in which one —CH$_2$CH$_2$— or —CH$_2$CH— group is replaced by a —CH=CH— or CH=C— group respectively
Z is a single bond
$R^2$ is hydrogen or a straight-chain or branched alkyl radical (with or without asymmetric carbon atoms) having 1 to 20 carbon atoms, where one nonterminal CH$_2$ group may be replaced by —O— or —OC(=O)— or —C(=O)O— and/or one or more H atoms may be replaced by F, with the proviso that the —CH$_2$— group nearest to the cyclopentene cannot be replaced and where
a is 1
b is 0 or 1
Y is —OC(=O)—, —OCH$_2$—

$R^1$ is hydrogen or a straight-chain or branched $C_{1-20}$-alkyl or $C_{2-20}$-alkenyl radical (with or without asymmetric carbon atoms), where
a) one or two nonterminal CH$_2$ groups may be replaced, independently of one another, by —O— or —C(=O)—, with the proviso that two adjacent CH$_2$ groups cannot be replaced in the same way, and/or
b) one CH$_2$ group may be replaced by —C≡C—, and/or
c) one CH$_2$ group may be replaced by —Si(CH$_3$)$_2$—, cyclopropane-1,2-diyl, cyclobutane-1,3-diyl, cyclopentane-1,4-diyl, bicyclo[1.1.1]pentane-1,3-diyl or cyclohexane-1,4-diyl, and/or
d) one or more H atoms may be replaced by F and/or CN,
e) in the case of a branched alkyl radical containing asymmetric carbon atoms, the asymmetric carbon atoms have —CH$_3$, —OCH$_3$, —CF$_3$, F, CN and/or Cl as substituents or are incorporated into a 3- to 7-membered ring, in which, in addition, one or two non-adjacent CH$_2$ groups may be replaced by —O— and one CH$_2$ group non-adjacent to these groups may be replaced by —OC(=O)—;

X is a single bond, —O—, OC(=O)—, —C(=O)O— or —OC(=O)O—;

$A^1$, $A^2$, $A^3$ are each, independently of one another, phenylene-1,4-diyl, unsubstituted or monosubstituted or disubstituted by CN or F, phenylene-1,3-diyl, unsubstituted or monosubstituted or disubstituted by CN or F, cyclohexane-1,4-diyl, in which one or two H atoms may be replaced by CN and/or $CH_3$ and/or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, cyclopentane-2,5-diyl or thiophene-2,5-diyl;

$M^1$, $M^2$ are undirected and are each, independently of one another, —OC(=O)—, —$OCH_2$—, —$CH_2CH_2$—, —OC(=O)$CH_2CH_2$—, —$OCH_2CH_2CH_2$—, —C≡C—, —$CH_2CH_2CH_2CH_2$— or a single bond;

wherein said liquid crystal mixture is ferroelectric (chiral smectic) and further comprises one or more compounds having a smectic phase.

12. The ferroelectric switching and/or display device of claim 7, which contains a liquid-crystal mixture comprising at least one compound of the formula (I):

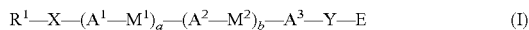

where the symbols and indices have the following meanings:

E is a radical T—Z—$R^2$ containing a five-membered ring, where:

(i) T is undirected and is 4-fluorothiophene-2,5-diyl, 3-fluorothiophene-2,5-diyl, 3-fluorothiophene-2,4-diyl or 5-fluorothiophene-2,4-diyl Z is a single bond or —O—

$R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, with the provisos that a) the —$CH_2$— group nearest to the thiophene cannot be replaced by —O— when Z is —O— b) $R^2$ can only be hydrogen when Z is a single bond,

Y is —OC(=O)—, —$OCH_2$—, —$CH_2CH_2$— a, b are each, independently of one another, 0 or 1

(ii) T is furan-2,5-diyl or furan-2,4-diyl

Z is a single bond or —O—

$R^2$ is a straight-chain or branched alkyl radical (with or without asymmetric carbon atoms) having 1 to 20 carbon atoms, where one nonterminal $CH_2$ group nonadjacent to furan maybe replaced by —O— or —OC(=O)— or —C(=O)O— and/or one or more H atoms may be replaced by F, Y is —OC(=O)—, —$OCH_2$—, —$CH_2CH_2$— a, b are each, independently of one another, 0 or 1

(iii) T is undirected and is isoxazole-3,5-diyl

Z is a single bond or —O—

$R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, with the provisos that a) the —$CH_2$— group nearest to the isoxazole cannot be replaced by —O— when Z is —O— b) $R^2$ can only be hydrogen when Z is a single bond, a is 1 b is 0 or 1

Y is —OC(=O)—, —$OCH_2$—, —$CH_2CH_2$—

(iv) T is undirected and is thiazole-2,4-diyl

Z is a single bond $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, Y is —OC(=O)—, —$OCH_2$—, —$CH_2CH_2$— a, b are each, independently of one another, 0 or 1

(v) T is cyclopentane-1,3-diyl, in which one —$CH_2CH_2$— or —$CH_2CH$— group is replaced by a —CH=CH— or CH=C— group respectively Z is a single bond $R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, with the proviso that the —$CH_2$— group nearest to the cyclopentene cannot be replaced and where a is 1 b is 0 or 1

Y is —OC(=O)—, —$OCH_2$—

$R^1$ is hydrogen or a straight-chain or branched $C_{1-20}$-alkyl or $C_{2-20}$-alkenyl radical (with or without asymmetric carbon atoms), where a) one or two nonterminal $CH_2$ groups may be replaced, independently of one another, by —O— or —C(=O)—, with the proviso that two adjacent $CH_2$ groups cannot be replaced in the same way, and/or b) one $CH_2$ group may be replaced by —C≡C—, and/or c) one $CH_2$ group may be replaced by —Si($CH_3$)$_2$—, cyclopropane-1,2-diyl, cyclobutane-1,3-diyl, cyclopentane-1,4-diyl, bicyclo[1.1.1]pentane-1,3-diyl or cyclohexane-1,4-diyl, and/or d) one or more H atoms may be replaced by F and/or CN, e) in the case of a branched alkyl radical containing asymmetric carbon atoms, the asymmetric carbon atoms have —$CH_3$, —$OCH_3$, —$CF_3$, F, CN and/or Cl as substituents or are incorporated into a 3- to 7-membered ring, in which, in addition, one or two non-adjacent $CH_2$ groups may be replaced by —O— and one $CH_2$ group non-adjacent to these groups may be replaced by —OC(=O)—;

X is a single bond, —O—, OC(=O)—, —C(=O)O— or —OC(=O)O—;

$A^1$, $A^2$, $A^3$ are each, independently of one another, phenylene-1,4-diyl, unsubstituted or monosubstituted or disubstituted by CN or F, phenylene-1,3-diyl, unsubstituted or monosubstituted or disubstituted by CN or F, cyclohexane-1,4-diyl, in which one or two H atoms may be replaced by CN and/or $CH_3$ and/or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, cyclopentane-2,5-diyl or thiophene-2,5-diyl;

$M^1$, $M^2$ are undirected and are each, independently of one another, —OC(=O)—, —$OCH_2$—, —$CH_2CH_2$—, —OC(=O)$CH_2CH_2$—, —$OCH_2CH_2CH_2$—, —C≡C—, —$CH_2CH_2CH_2CH_2$— or a single bond;

wherein said liquid crystal mixture is nematic and further comprises one or more compounds having a nematic phase.

* * * * *